United States Patent
Hochberg et al.

(10) Patent No.: US 8,556,993 B2
(45) Date of Patent: Oct. 15, 2013

(54) LAUNDERING PROCESS FOR WHITENING SYNTHETIC TEXTILES

(75) Inventors: Robert Hochberg, Merzhausen (DE); Oliver Becherer, Schwörstadt (DE); Bernard Schultz, St. Louis (FR); Goetz Scheffler, Grenzach-Wyhlen (DE); René Schlatter, Lörrach (DE)

(73) Assignee: BASF SE, Ludwigshafen (DE)

( * ) Notice: Subject to any disclaimer, the term of this patent is extended or adjusted under 35 U.S.C. 154(b) by 257 days.

(21) Appl. No.: 11/922,070

(22) PCT Filed: Jun. 7, 2006

(86) PCT No.: PCT/EP2006/062950
§ 371 (c)(1),
(2), (4) Date: Aug. 13, 2009

(87) PCT Pub. No.: WO2006/134044
PCT Pub. Date: Dec. 21, 2006

(65) Prior Publication Data
US 2009/0293210 A1    Dec. 3, 2009

(30) Foreign Application Priority Data

Jun. 15, 2005  (EP) ................... 05105274
Jun. 20, 2005  (EP) ................... 05076443

(51) Int. Cl.
*C11D 3/37*  (2006.01)
*C11D 3/42*  (2006.01)
*C11D 3/60*  (2006.01)

(52) U.S. Cl.
USPC .......... 8/137; 8/552; 8/554; 8/648; 252/8.91; 510/276; 510/337; 510/324; 510/394; 510/516; 510/475

(58) Field of Classification Search
USPC .......... 8/648, 101, 107, 137, 137.5, 552, 554; 252/8.91; 510/276, 337, 324, 394, 516, 510/475

See application file for complete search history.

(56) References Cited

U.S. PATENT DOCUMENTS

| | | | |
|---|---|---|---|
| 3,193,548 A | | 7/1965 | Crounse et al. ............... 260/240 |
| 3,951,965 A | | 4/1976 | Mengler et al. ............... 260/240 |
| 4,418,011 A | * | 11/1983 | Bauman et al. ............... 510/325 |
| 4,761,249 A | * | 8/1988 | Giede et al. ....................... 8/137 |
| 4,946,628 A | | 8/1990 | Schüssler et al. .............. 252/543 |
| 4,964,628 A | * | 10/1990 | Poplawski ....................... 482/51 |
| 5,167,871 A | * | 12/1992 | Jollenbeck et al. ........... 510/325 |
| 5,234,617 A | | 8/1993 | Hunter et al. .................. 252/102 |
| 5,891,837 A | * | 4/1999 | Baillely et al. ................ 510/309 |
| 2003/0109408 A1 | * | 6/2003 | Brouwn et al. ............... 510/424 |
| 2007/0225184 A1 | * | 9/2007 | Rohwer et al. ................ 510/103 |

FOREIGN PATENT DOCUMENTS

| | | | |
|---|---|---|---|
| DE | 298198 | | 2/1992 |
| GB | 2287949 | | 10/1995 |
| WO | WO 01/53600 | * | 7/2001 |
| WO | 2004/046293 | | 6/2004 |

OTHER PUBLICATIONS

Seong-Il Um et al., Dyes and Pigments, vol. 64, (2005), pp. 93-99.
H. Häusermann et al., Textil-Rundschau, vol. 16, (1961), pp. 176-178.
P. S. Patel et al., Asian Journal of Chemistry, vol. 11, No. 3, (1999), pp. 800-804.

* cited by examiner

*Primary Examiner* — Lorna M Douyon
*Assistant Examiner* — Amina Khan
(74) *Attorney, Agent, or Firm* — Shiela A. Loggins

(57) ABSTRACT

The present invention relates to the use of a combination of a free fluorescent whitening agent and cationic polymer as a brightening agent for a synthetic single or blended textile, especially polyester textile, and to a corresponding brightening agent as well as a laundering process for brightening a synthetic, single or blended textile, which is characterized by a) preparing a composition by contacting a free fluorescent whitening agent with a cationic polymer, and b) treating said synthetic, single or blended textile with the composition prepared in step a).

11 Claims, No Drawings

LAUNDERING PROCESS FOR WHITENING SYNTHETIC TEXTILES

The present invention relates to the use of a free fluorescent whitening agent and a cationic polymer in a laundering process for brightening a synthetic, single or blended textile, to novel fluorescent whitening agents, and to novel brightening compositions.

Usually, synthetic textile, especially polyester, is brightened during its process of preparation or dyeing, wherein high temperatures from about 120° C. are applied. There is still a demand to brighten polyester also in domestic laundering processes, where only lower temperatures from 30 to 60° C. are applicable.

The problem underlying the present invention is to find a process for the domestic brightening of synthetic and especially polyester fabric. It has been found that, surprisingly, a combination of a free flowing fluorescent whitener and a cationic polymer, when added to the wash cycle, achieves an excellent brightening effect on synthetic textiles, especially those based on polyester.

Thus, the present invention primarily pertains to the use of a combination of a free fluorescent whitening agent and cationic polymer as a brightening agent for a synthetic single or blended textile.

The laundering process leads to brightening of the synthetic, single or blended textile, especially polyester or polyamide textiles or polyester or polyamide blended textiles, wherein the blended textile preferably comprises at least 40% by weight, preferably at least 50% by weight, of polyester or polyamide. The process is characterized by
a) preparing a composition by bringing into contact a free fluorescent whitening agent with a cationic polymer, and
b) treating said synthetic, single or blended textile with the composition prepared in step a).

In the general context of the present invention, a laundering process covers all processes, wherein detergents and/or softeners are used. Especially preferred is the first or second wash cycle, wherein the textile is treated with a detergent and water in liquor ratio such as 1:4 or higher and in a temperature range of below 100° C., especially about 10 to about 60° C.

In the context of the present invention, the fluorescent whitening agent employed is a free fluorescent whitener, i.e. free molecular compound used as such or used in a mixture with other compounds, in non-encapsulated form.

Suitable fluorescent whitening agents preferably are amphiphilic, i.e. they are boundary surface-active with a certain solubility in aqueous media and in apolar media.

Amphiphilic has in the context of the present invention the following meaning:
Amphiphile fluorescent whitening agents contain a polar (hydrophilic) and an apolar (hydrophobic) moiety. At a phase boundary (e.g. surface of an aqueous medium), they may form a monomolecular film, or micelles in aqueous phases, or arrange to bilayer diaphragm.

Suitable synthetic textile is, for example, polyester, polyamide, polyacrylonitrile, polyacryl, polyisoprene or polyurethane. Preferred synthetic textile fabric is polyester or polyamide, more preferred is polyester.

Suitable blended textile is synthetic or natural.

Suitable natural textiles include vegetable fibres such as cotton, viscose, flax, rayon or linen, preferably cotton and animal fibres such as wool, mohair, cashmere, angora and silk, preferably wool.

Preferred synthetic blended textile is blended polyester or polyamide, more preferred is polyester.

Preferred blended polyester is polyester/cotton and polyester/polyamide.

Preferably, the ratio by weight of synthetic to natural fabric, especially polyester to cotton, in a blended textile is 80:20 to 20:80, more preferably 70:30 to 30:70.

Preferred is a laundering process, which is characterized by
a) introducing a fluorescent whitening agent and a cationic polymer in water, and optionally
b) contacting the watery liquid prepared in step a) with said synthetic, single or blended textile.

Preferred fluorescent whitening agents according to the present invention correspond to formula (1)

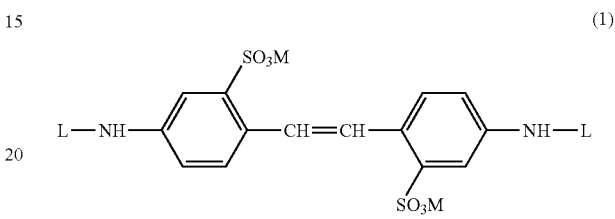

wherein
L is a radical of formulae (2) or (3)

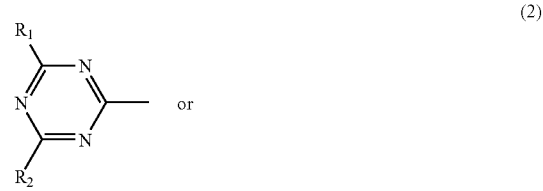

wherein
$R_1$ and $R_2$ are independently from each other a substituted or unsubstituted aryloxy;
or a saturated or unsaturated, interrupted or uninterrupted substituted or unsubstituted aliphatic cycloaliphatic or aliphatic alkoxy or aralkyloxy;
or a hydroxy or chloride radical; or
a substituted or unsubstituted amine; and
$R_3$ and $R_4$ are independently from each other hydrogen or a substituted or unsubstituted, branched, unbranched, interrupted or uninterrupted alkyl radical or a substituted or unsubstituted carbocylic or heterocyclic aryl radical, and
M is a cation.

Preferred is the process according to the present invention, wherein the fluorescent whitening agent is of formula (1), wherein L is a radical of formula (2) and wherein $R_1$ and $R_2$ are independently from each other an amine.

Suitable substituted amine is, for example, substituted, unsubstituted, saturated or unsaturated, branched, unbranched, interrupted or uninterrupted alkylamine, alkylenamine, di-alkylamine, dialkylenamine, N-alkyl-arylamine, N-alkylen-arylamine, N-alkylene-arakylamine or N-alkyl-aralkylamine; or substituted or unsubstituted aryl or aralkyl or N-aryl-aralkylamine; or interrupted or uninterrupted, saturated or unsaturated aliphatic cycloaliphatic alkylamine.

Suitable substitutents of substituted amine are, for example, hydroxy, carboxy, cyano, amido, alkoxy, trialkoxy-trisiloxanyl, alkylguanidinyl or aryl, especially by hydroxy, aryl or carboxy.

Preferred substituted amine is, for example, substituted, unsubstituted, saturated or unsaturated, branched, unbranched, interrupted or uninterrupted $C_6$-$C_{40}$alkylamine, di-$C_1$-$C_4$alkylamine, hydroxy-$C_1$-$C_4$alkylamine, N—$C_1$-$C_4$alkyl-hydroxy-$C_1$-$C_4$alkylamine, di-hydroxy-$C_1$-$C_4$alkylamine, N-aryl-aralkylamine, N-alkyl-alkylguanidinylamine, alkylguanidinylamine, N-alkyl-alkyletheramine, alkylpolyalkyletheramine or a (tri-alkoxy)-trisiloxanylalkylamine radical; or interrupted or uninterrupted, saturated or unsaturated aliphatic cycloaliphatic alkylamine, preferably cyclohexylamine, pyrrolidine, piperidine, piperazine, morpholine, and more preferably cyclohexylamine and morpholine; or substituted or unsubstituted arylamine, preferably phenylamine, aralkylamine, preferably benzylamine or phenylethylamine, or N-aryl-aralkylamine, preferably N-phenyl-benzylamine.

Examples of substituted amine are —$NHCH_3$, —$NHC_2H_5$, —$NH(n-C_3H_7)$, —$NH(i-C_3H_7)$, —$NH(i-C_4H_9)$, —$N(CH_3)_2$, —$N(C_2H_5)_2$, —$N(i-C_3H_7)_2$, —$NH(CH_2CH_2OH)$, —$N(CH_2CH_2OH)_2$, —$N(CH_2CH(OH)CH_3)_2$, —$N(CH_3)(CH_2CH_2OH)$, —$N(C_2H_5)(CH_2CH_2OH)$, —$N(i-C_3H_7)(CH_2CH_2CH_2OH)$, —$NH(CH_2CH(OH)CH_3)$, —$N(C_2H_5)(CH_2CH(OH)CH_3)$, —$NH(CH_2CH_2OCH_3)$, —$NH(CH_2CH_2OCH_2CH_2OH)$, —$NH(CH_2COOH)$, —$NH(CH_2CH_2COOH)$, —$N(CH_3)(CH_2COOH)$, —$NH(CN)$, —$NH(C_6H_5)$, —$NH(C_6H_{13})$, —$NH(CH_2C_6H_5)$, —$NH(CH_2CH_2C_6H_5)$, —$NH(C_8H_{17})$, —$NH(CH_2CH_2CH_2OCH_2CH_2CH_2CH_3)$, —$NH(CH_2CH_2CH_2N(CH_2CH_3)_2)$, —$NH((CH_3)CH_2CH_2O)_{10}CH_3)$, —$NH(C_{16}H_{33})$, —$NH(C_{18}H_{37})$, —$NH(C_6H_{11})$, —$NH(C_7H_{14}CHCHCH_8CH_{17})$, —$N(CH_2C_6H_5)(C_6H_5)$, —$NH(CH_2CH_2CH_2N(CH_2CH_3)_2)$, —$NH(CH_2CH_2CH_2Si(OCH_3)_3)$,

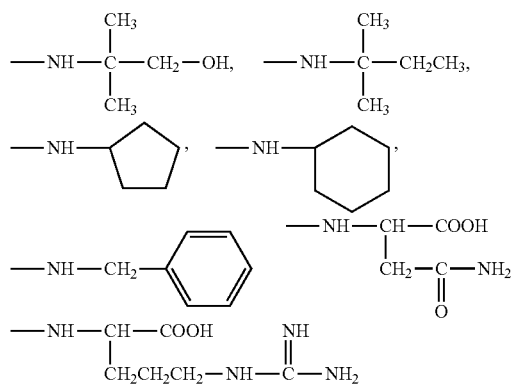

Preferred fluorescent whitening agents of formula (1) are those, wherein L is a radical of formula (2), and wherein the fluorescent whitening agent is of formula (1), wherein L is a radical of formula (2) and wherein $R_1$ is substituted or unsubstituted arylamine, aralkylamine, N-alkyl-arylamine, N-alkylen-arylamine, N-alkyl-aralkylamin, N-alkylen-aralkylamine or N-aryl-aralkylamine; and $R_2$ is substituted, unsubstituted, saturated or unsaturated, branched, unbranched, interrupted or uninterrupted $C_6$-$C_{40}$alkylamine, $C_6$-$C_{40}$alkylenamine, di-$C_1$-$C_6$alkylamine, di-$C_1$-$C_6$alkylenamine, N—$C_1$-$C_6$alkyl-arylamine, N—$C_1$-$C_6$alkylen-arylamine, N—$C_1$-$C_6$alkylen-aralkylamine or N—$C_1$-$C_6$alkyl-aralkylamine; substituted or unsubstituted arylamine, aralkylamine or N-aryl-aralkylamine; a saturated or unsaturated, interrupted or uninterrupted substituted or unsubstituted aliphatic, cycloaliphatic alkylamine.

Many of the free fluorescent whitening agents as described above are known compounds and commercially available, e.g. as single compounds or as mixtures or formulations as described further below.

Of specific interest is a process according to the present invention, wherein the fluorescent whitening agent used is a novel compound corresponding to the formula (30)

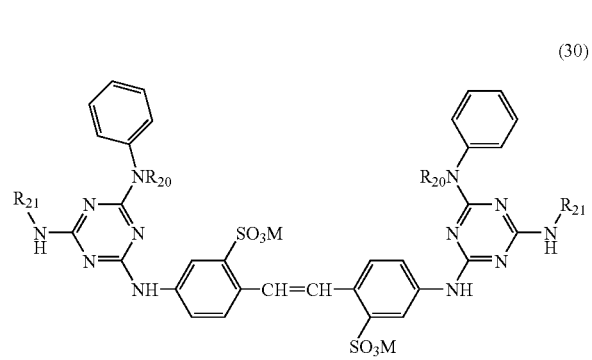

wherein
$R_{20}$ is hydrogen, or substituted or unsubstituted aryl, aralkyl or N-aryl-aralkyl; and
$R_{21}$ is substituted, unsubstituted, saturated or unsaturated, branched, unbranched, interrupted or uninterrupted $C_6$-$C_{40}$alkyl, $C_6$-$C_{40}$alkylen, $C_1$-$C_6$dialkyl, $C_1$-$C_6$dialkylen; substituted or unsubstituted aralkyl; and
M is a cation.

Compounds of the formula (30) may be generally obtained in analogy to methods known in the art, e.g. by reacting suitable salts of diaminostilbendisulfonic acid with cyanuric chloride, reacting the product obtained with a suitable aniline, and transferring the intermediate thus obtained with amine $R_{21}$—$NH_2$ into the desired end product. Reaction conditions and workup follow the conventional routes.

Cationic polymers suitable in the present invention often contain nitrogen.

Cationic polymers of the present invention may be homo-, hetero-, linear or crosslinked polymers.

Cationic polymers suitable in the present invention are cationic condensation and/or addition polymers, which may be homo-, hetero-, linear or crosslinked.

Suitable cross-linked polymers comprise a crosslinking agent comprising, for example, polyethylenic functions.

Suitable cationic polymers may be selected from cationic derivatives of starch, cellulose ether, especially hydroxyethyl cellulose, polyester, polyether, polyurethan, polyamides, polyamine, polyimine, polyurea, polyalkenylcarboxylate, especially polyacrylate or polymethacrylate, polyalkenylhydroxy carbonyl, especially polyvinylacetate, polyalkenylamine carbonyl, especially polyvinylamine carbonyl, polyalkenylamide, especially polyacrylamide, polyalkenoyl, polyalkenylether, especially polyvinylether, polyalkenyloyl, especially polyvinyloyl, polyalkylenoxid, especially polyethylenoxid, polyvinylpyrrolidon, polyvinyl-imidazol, polymer comprising copolymers of N-vinylpyrrolidon and N-vinylimidazole, poly-amine-N-oxide, polyamine, especially polyethylamines or poly-dimethylallylammonium-halogenide, especially poly-dimethylallylammoniumchloride (Poly-DADMAC), polyimine, especially polyethylimines, and mixtures thereof.

Preferred cationic polymers have a molecular weight within the range from about 2,000 to about 30,000,000.

Further preferred cationic polymers have a cationic charge density greater than 0.001 in an aqueous solution.

The "cationic charge density" of a polymer as that term is used herein refers to the ratio of the number of positive charges on a monomeric unit of which the polymer is comprised to the molecular weight of said monomeric unit, i.e., $$\text{cationic charge density} = \frac{\text{number of positive charges}}{\text{monomeric unit molecular weight}}$$

The cationic charge density multiplied by the polymer molecular weight determines the number of positively charged active sites on a given polymer chain.

Preferably the cationic polymers are water-soluble.

Preferred cationic polymers comprising at least one preferred cationic monomer unit either of formula

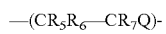
—(CR$_5$R$_6$—CR$_7$Q)- wherein
each of R$_5$, R$_6$, R$_7$ is independently selected from hydrogen, substituted or unsubstituted C$_1$-C$_4$ alkyl, optionally substituted phenyl, optionally substituted benzyl, carbocyclic and heterocyclic groups, and
Q is selected from groups of formula

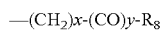
—(CH$_2$)x-(CO)y-R$_8$ wherein
x is 0 to 6 and y is 0 or 1,
R$_8$ being selected from —O(CH$_2$)$_z$N$^+$(R$_9$)$_3$X$^-$, —OCO(CH$_2$)$_z$N$^+$(R$_9$)$_3$X$^-$, —NHCO(CH$_2$)$_z$N$^+$(R$_9$)$_3$X$^-$, —(CH$_2$)$_z$N$^+$(R$_9$)$_3$X$^-$, nitrogen heterocyclic quaternary ammonium, nitrogen heterocyclic N-oxide, aromatic N-heterocyclic quaternary ammonium, aromatic N-heterocyclic N-oxide;
wherein
z is from 0 to 6,
X$^-$ is a water soluble cation such as an alkaline metal ion, and
R$_9$ is selected from hydrogen, C$_1$-C$_8$alkyl and C$_2$-C$_8$ hydroxyalkyl; or derived from monomers of formula:

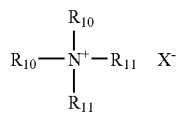

wherein
each R$_{10}$ is independently an olefin comprising unit which is capable of propagating polymerization in addition to forming a cyclic residue with an adjacent R$_{10}$ unit;
each R$_{11}$ is linear or branched C$_1$-C$_{12}$alkyl, benzyl, substituted benzyl.

Preferred monomer units carrying at least one positive charge contain heterocyclic N—R$_5$-R$_{12}$ moieties where the nitrogen atom is quaternized and R$_{12}$ is independently selected from carboxylate and sulphonate and R$_5$ is defined as given above.

Preferred monomer units are cyclic moieties containing one or more heteroatoms such as nitrogen and having one or more unsaturated bonds either within the ring or attached to the ring, e.g. pyrrolidone, imidazole and mixtures thereof.

Preferred co-monomers for copolymerization with the preferred cationic monomer units defined above are those of formula —(CR$_5$R$_6$—CR$_7$R$_{12}$), wherein
R$_5$-R$_7$ are as hereinbefore defined and R$_{12}$ is independently selected from hydroxy, and groups as hereinbefore defined for any of R$_5$-R$_7$ and groups of formula

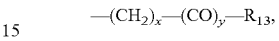
—(CH$_2$)$_x$—(CO)$_y$—R$_{13}$, wherein
x is 0 to 6 and y is 0 or 1, and
R$_{13}$ is selected from hydrogen, hydroxyl, halogen, nitrilo, —OR$_3$, —O(CH$_2$)$_x$N(R$_9$)$_2$, —OCO(CH$_2$)$_x$N(R$_9$)$_2$, —NHCO(CH$_2$)$_x$N(R$_9$)$_2$, —(CH$_2$)$_x$N(R$_9$)$_2$, carbocyclic, heterocyclic, —NHCHO,
wherein z is from 0 to 6, and R$_9$ is as defined above.

These polymers are commercially available or may be prepared as described in WO-A-01/53600.

Further, preferred co-monomers for copolymerization with the preferred cationic monomer units defined above are derivatives of N-vinyl pyrrolidone, N-vinyl imidazole or styrene. alkenyloxy alkylester, especially vinylacetat, alkenoyl alkylamide, especially vinoyl alkylamide, alkenylamide, especially acrylamide, alkenoyl, alkenylether, especially vinylether, alkenyloyl, especially, vinyloyl, alkylenoxid, especially ethylenoxid, N-vinylpyrrolidons, N-vinylimidazols, amine-N-oxide, amines, especially ethylamines or amine with allylhalide, and mixtures thereof.

In addition, preferred polymers for reaction with the preferred cationic monomer units defined above are derivatives of cellulose or starch, especially derivatives of hydroxyethylcellulose.

Examples of cationic polymers include the following commercially available materials CROSCOLOR PMF (July 1981, Code No. 7894) and CROSCOLOR NOFF (January 1988, Code No. 8544) ex Crosfield; INDOSOL E-50 (Feb. 27, 1984, Ref. No. 6008.35.84; polyethyleneamine-based) ex Sandoz; SANDOFIX TPS, ex Sandoz, is a preferred dye fixative for use herein. Additional non-limiting examples include SANDOFIX SWE (a cationic resinous compound) ex Sandoz, REWIN SRF, REWIN SRF-O and REWIN DWR ex CHT-Beitlich GMBH; Tinofix® ECO, Tinofix® FRD and Solfin® ex Ciba-Geigy. A preferred dye fixing agent for use in the compositions of the present invention is CARTAFIX CB® ex Clariant. Other cationic dye fixing agents are described in "Aftertreatments for Improving the Fastness of Dyes on Textile Fibres", Christopher C. Cook, Rev. Prog. Coloration, Vol. XII.

Further, preferred polymers are polyvinylpyrrolidone (PVP) and polyvinylpyrrolidone/polyvinylimidazole (PVP/PVI) as described in WO-A-97/23591 and WO-A-97/23592.

More preferred cationic polymers are derivatives of polyarylate, cellulose and polyamines as defined hereinbefore.

Most preferred cationic polymers are those of formulae (25), (26) and (27)

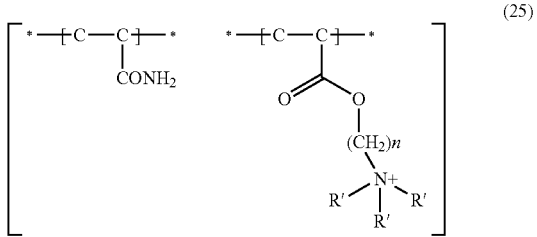

(25)

wherein
n is interrupted or uninterrupted, substituted or unsubstituted, branched or unbranched $C_1$-$C_{30}$alkyl, and
R' is $C_1$-$C_4$alkyl,

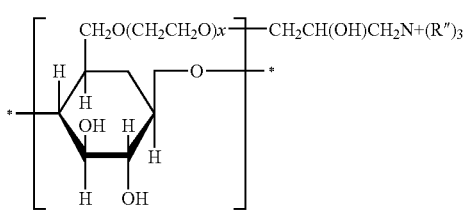

(26)

wherein
x is, and
R" is $C_1$-$C_4$alkyl,

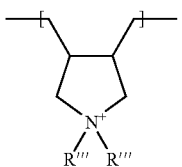

(27)

wherein
R''' is $C_1$-$C_4$alkyl.

In general, cationic polymers as described above are known in the art; many are commercially available.

The terms and expressions used in the description of the invention preferably have the following meanings:

Suitable substituents of $R_1$, $R_2$, $R_3$ and $R_4$ may be selected, for example, from the group of functional groups or derivatised functional groups consisting of alkyl, aryl, alkoxy, alkylthio, halogen, hydroxy, sulphinester, carboxylic ester, carboxylic amide, amine, alkylamine, dialkylamine, cyano, polyalkoxy,
which may themselves be combined as desired with further such radicals and substituted by the mentioned functional groups or derivatised functional groups.

The mentioned substituents and radicals may also be interrupted by one or more bivalent radicals from the group —O—, —S—, —C(=O)O—, —O—C(=O)—, —C(=O)—N($C_1$-$C_4$alkyl)-, —N($C_1$-$C_4$alkyl)-C(=O)—, —S(=O)—, —S(=O)$_2$—, —S(=O)—O—, —S(=O)$_2$—O—, —O—S(=O)—, —O—S(=O)$_2$—, —S(=O)—N($C_1$-$C_4$alkyl)-, —S(=O)$_2$—N($C_1$-$C_4$alkyl)-, —($C_1$-$C_4$alkyl) N—S(=O)—, —($C_1$-$C_4$alkyl)N—S(=O)$_2$—, —P(=O)—, —P(=O)—O—, —O—P(=O)— and —O—P(=O)—O—. Preferred radical for interruption is —O—. Examples are —$C_3H_6$—O—$C_5H_{11}$, or —($CH_2(CH_3)CH_2$—O)$_{10}$—$CH_3$ Alkyl is preferably $C_6$-$C_{40}$alkyl, preferably or $C_1$-$C_4$.

Definitions given for alkyl correspond in analogy to all expressions comprising alkyl, such as alkyloxy, alkylthio, aralkyl or alkylamine and to alkylen and all expressions comprising alkylen.

$C_6$-$C_{40}$Alkyl is, for example, hexyl, heptyl, octyl, isooctyl, nonyl, tert-nonyl, decyl, undecyl or dodecyl, hexadecyl, ocatdecyl or tertacontan.

$C_1$-$C_{12}$alkyl is, for example, methyl, ethyl, n- or iso-propyl or n-, sec- or tert-butyl or straight-chain or branched pentyl, hexyl, heptyl, octyl, isooctyl, nonyl, tert-nonyl, decyl, undecyl or dodecyl.

$C_1$-$C_8$alkyl is, for example, methyl, ethyl, n- or iso-propyl or n-, sec- or tert-butyl or straight-chain or branched pentyl, hexyl, heptyl or octyl.

$C_1$-$C_4$Alkyl is, for example, methyl, ethyl, n- or iso-propyl or n-, sec- or tert-butyl.

$C_2$-$C_{20}$Alkenyl is, for example, vinyl, allyl, 2- or 3-butenyl, isobutenyl or n-penta-2,4-dienyl.

$C_2$-$C_{20}$Alkynyl is, for example, 1- or 2-propynyl.

Alkoxy is preferably $C_1$-$C_8$alkoxy and more preferably $C_1$-$C_4$alkoxy.

$C_2$-$C_8$ Hydroxyalkyl is, for example, hydroxyethyl, n- or iso-hydroxypropyl or n-, sec- or tert-hydroxybutyl or straight-chain or branched hydroxypentyl, hydroxyhexyl, hydroxyheptyl, hydroxyoctyl, iso hydroxyoctyl, Cycloaliphatic alkyl may be a saturated or unsaturated bicycloalkyl, or monocycloalkyl, hetero- or carbocyclic.

Preferred monocyclo alkyl is, $C_3$-$C_{12}$Cycloalkyl.

$C_3$-$C_{12}$Cycloalkyl is, for example, cyclopropyl, dimethylcyclopropyl, cyclobutyl, cyclopentyl or cyclohexyl, and preferably $C_3$-$C_{12}$Cycloalkyl.

Preferred bicycloalkyl is $C_7$-$C_{12}$Bicycloalkyl.

$C_7$-$C_{12}$Bicycloalkyl is, for example, bornyl or norbornyl.

Preferred unsaturated monocycloalkyl is $C_4$-$C_{12}$Cycloalkenyl.

$C_4$-$C_{12}$Cycloalkenyl is, for example, cyclopentadienyl or cyclohexenyl.

Preferred heterocycloalkyl is $C_2$-$C_{11}$heterocycloalkyl.

$C_2$-$C_{11}$Heterocycloalkyl preferably contains 4 or 5 carbon atoms and one or two hetero atoms from the group O, S and N. Examples are the substituents derived from oxirane, azirine, 1,2-oxathiolane, pyrazoline, pyrrolidine, piperidine, piperazine, morpholine, tetrahydrofuran or tetrahydrothiophene, and preferably morpholine.

Aryl may be carbocyclic or heterocyclic aryl.

Definitions given for aryl correspond in analogy to all expressions comprising aryl, such as aryloxy, arlthio, aralkyl or arlamine.

Preferred is $C_6$-$C_{16}$aryl.

$C_6$-$C_{16}$aryl is, for example, mono-, bi- or tricyclic, for example phenyl, naphthyl, indenyl, azulenyl or anthryl.

Preferred heterocyclic aryl is $C_2$-$C_{15}$heteroaryl.

$C_2$-$C_{15}$heteroaryl is preferably monocyclic or condensed with a further heterocycle or with an aryl radical, for example phenyl, and preferably contains one or two, and in the case of nitrogen up to four, hetero atoms from the group O, S and N. Suitable substituents are derived from furan, thiophene, pyrrole, pyridine, bipyridine, picolylimine, pyran, thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, isoquinoline, acridine, chromene, phenazine, phenoxazine, phenothiazine, triazine, thianthrene, purine or tetrazole.

Aralkyl is preferably $C_7$-$C_{16}$aralkyl.

$C_7$-$C_{16}$aralkyl preferably contains from 7 to 12 carbon atoms, for example benzyl, 1- or 2-phenethyl or cinnamyl.

The cation M is preferably hydrogen or an alkaline metal atom, an alkaline earth metal atom, ammonium or a cation formed from an amine. Preferred are Na, K, Ca, Mg, ammonium, mono-, di-, tri- or tetra-$C_1$-$C_4$alkylammonium, mono-, di- or tri-$C_2$-$C_4$-hydroxyalkylammonium or ammonium that is di- or tri-substituted with a mixture of $C_1$-$C_4$-alkyl and $C_2$-$C_4$-hydroxyalkyl groups. Highly preferred is sodium.

Halogen may be fluorine, chlorine, bromine or iodine, preferably chlorine.

In the context of the present invention a laundry composition is a detergent composition or a softening composition, which may be optionally liquid.

As noted above, the free fluorescent whitening agent used in the present invention is a molecular compound which is used as such in non-encapsulated form. It may be a single compound or a mixture of different fluorescent whiteners. The free fluorescent whitening agent often is employed as a mixture containing the free fluorescent whitener along with other compounds, such as salts or formulation aids explained below. It may be a solid or liquid formulation.

Formulations containing a fluorescent whitening agent and processes of their preparation are well known in the prior art and encompassed by the scope of the present invention.

Suitable storage-stable formulations are for example described in U.S. Pat. No. 5,076,968, U.S. Pat. No. 5,518,657, U.S. Pat. No. 5,429,767, or suitable further components, such as, for example, sequestering agents, stabiliser, dispersing, emulsifising agents or optionally auxiliaries of a formulation are described in U.S. Pat. No. 5,076,968, U.S. Pat. No. 5,518,657, U.S. Pat. No. 5,437,818, U.S. Pat. No. 5,429,767, U.S. Pat. No. 5,622,749, U.S. Pat. No. 5,695,687, U.S. Pat. No. 6,153,123, U.S. Pat. No. 6,133,215 and U.S. Pat. No. 6,660,705.

Suitable solid formulations of a fluorescent whitening agent comprise, for example, salts, such as anorganic or organic salts.

Suitable anorganic salts are alkaline metal chloride, alkaline metal sulfate, alkaline metal carbonate, alkaline metal phosphate or earth alkaline metal chloride, earth alkaline metal sulfate or earth alkaline metal carbonate, earth alkaline metal phosphate or mixtures thereof.

Suitable liquid formulations of the fluorescent whitening agent comprise, for example, dispersing agents, emulsifising agents, polysaccharides, especially non-ionic or anionic polysaccharides, electrolytes, stabilizers, surfactants, especially non-ionic or anionic surfactants, preservatives, fabric softeners, anti-redeposition agents, and optional auxiliaries, such as, for example, antifoam agents, alkaline agents, fabric softeners, anti-redeposition agents, antioxidants, auxiliary builders such as polyacrylic acid and fragrances, organic solvents such as glycols, e.g., ethylene glycol, glycol-$C_1$-$C_4$ alkyl ethers or -esters.

Suitable dispersing agents are, for example, anionic or non-ionic. Examples are alkylbenzenesulfonates, alkyl or alkenyl ether sulfonates salts, saturated or unsaturated fatty acids, alkyl or alkylene ether carboxylate salts, sulfonated fatty acid salts or esters, phosphate esters, polyoxyethylene alkyl or alkenyl ethers, polyoxyethylene alkyl vinyl ethers, polyoxypropylene alkyl or alkenyl ethers, polyoxybutylene alkyl or alkenyl ethers, higher fatty acid alkanolamides or alkylene oxide adducts, sucrose/fatty acid esters, fatty acid/glycol monoesters, alkylamine oxides and condensates of aromatic sulfonic acids with formaldehyde, as well as lignin-sulfonates or mixtures of the above cited dispersants. Non-ionic surfactants, such as polyoxyethylene alkyl or alkenyl ethers, polyoxyethylene alkyl vinyl ethers, polyoxypropylene alkyl or alkenyl ethers, polyoxybutylene alkyl or alkenyl ethers, higher fatty acid alkanolamides or alkylene oxide adducts, especially lower ethylene oxide adducts with fatty alcohols, are preferred.

Suitable emulsifising agents are, for example, anionic or non-ionic.

Examples of anionic emulsifiers which may be mentioned are:

Carboxylic acids and their salts, such as the sodium, potassium or ammonium salts of lauric, stearic or oleic acid, acylation products of aminocarboxylic acids and their salts, for example the sodium salt of oleoylsarcoside, sulfates, such as fatty alcohol sulfates, for example lauryl sulfate and coconut sulfate, sulfates of hydroxy fatty acid esters, for example sulfated castor oil, and of fatty acid hydroxyalkylamides, for example sulfated coconut oil acid ethanolamide, and sulfates of partially esterified or etherified polyhydroxy compounds such as sulfated oleic acid monoglyceride or glycerol ether-sulfates, and furthermore sulfates of substituted polyglycol ethers, for example nonylphenyl polyglycol ether sulfate, sulfonates, such as primary and secondary alkylsulfonates, for example $C_{12}$-$C_{16}$ paraffinsulfonic acids and sodium salts thereof, alkylsulfonates with acyl radicals bonded in amide or ester form, such as oleyl-methyl-tauride, and sulfonates of polycarboxylic acid esters, such as diisooctylsulfatosuccinic acid esters; and furthermore those with aromatic groups such as alkylbenzene, for example dodecylbenzene-, alkylnaphthalene-, such as dibutylnaphthlene, and alkylbenzimidazole, such as tetradecylbenzimidazole-sulfonates.

Examples of non-ionic emulsifiers which may be mentioned are:

Esters and ethers of polyalcohols, such as alkyl polyglycol ethers, for example lauryl alcohol or oleyl alcohol, polyethylene glycol ethers, acyl polyglycol ethers, such as oleic acid polyglycol ether, alkylaryl polyglycol ethers, such as the ethoxylation products of nonyl- and dodecylphenol, acylated amino-alkanol polyglycol ethers, and furthermore the known non-ionic surfactants which are derived from fatty amines, such as stearylamine, fatty acid amides or sugars and derivatives thereof.

Suitable polysaccharide is, for example, xanthan or sodium-carboxymethylcellulose, preferably xanthan.

Preferably, polysaccharide is used in the liquid formulations in amounts of 0.01 to 1% by weight, especially in amounts of 0.05 to 0.5% by weight, related to the total weight of the formulation.

Suitable electrolytes are, for example, alkaline metal chloride, alkaline metal sulfate, alkaline metal carbonate or earth alkaline metal chloride, earth alkaline metal sulfate or earth alkaline metal carbonate or mixtures thereof.

Preferably, elektrolytes are used in the liquid formulations in amounts of 0.1 to 25% by weight, especially in amounts of 0.1 to 20% by weight, related to the total weight of the formulation.

Suitable stablisier is any material which is effective in adjusting the flow properties of and/or inhibiting sedimentation. Examples of such stabilizers include, e.g. kaolin, an Mg/Al silicate, especially bentonite, montmorillonite, a zeolite or a highly dispersed silicilic acid.

A non-ionic surfactant is preferably an alkoxylated fatty acid alcohol, especially ethoxylated and is, more preferably, a $C_8$-$C_{18}$-fatty acid alcohol which is ethoxylated with between 3 and 20 moles of ethylene oxide, a $C_{11}$-$C_{13}$-fatty acid alcohol which is ethoxylated with between 3 and 20 moles of ethylene oxide being most preferred, whereby a $C_{13}$-fatty acid alcohol which is ethoxylated with 9 moles of ethylene oxide (Marlipal O13/90) being the component of choice.

In a further preferred embodiment of the present invention, the cationic polymer and the free fluorescent whitening agent are added to the liquor at initiating a wash cycle.

More preferably, the wash cycle is initiated by introducing on 100 parts by weight of cationic polymer 0.1 to 1000 parts by weight, preferably 10 to 200 parts by weight, of free fluorescent whitening agent.

Most preferred is a use according to the present invention, wherein the fluorescent whitening agent is selected from formulae (4) to (19)

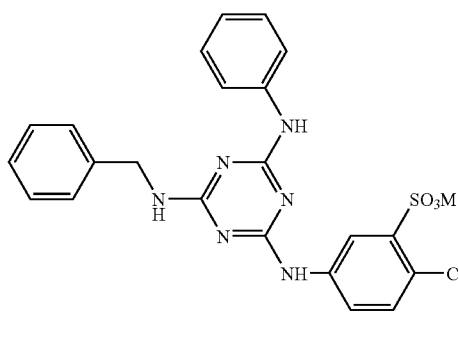
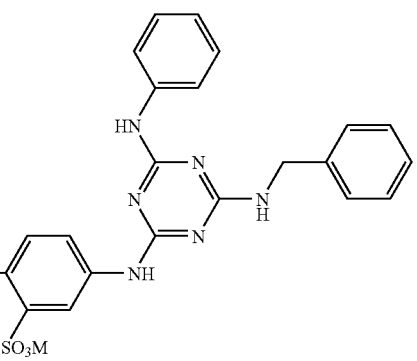

(4)

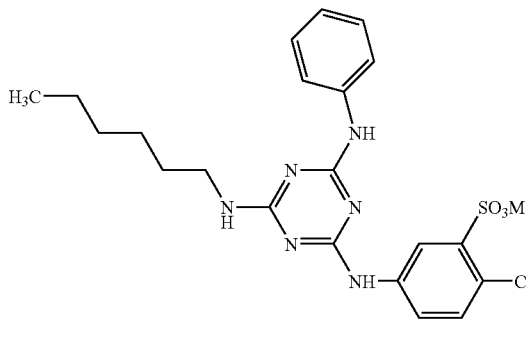
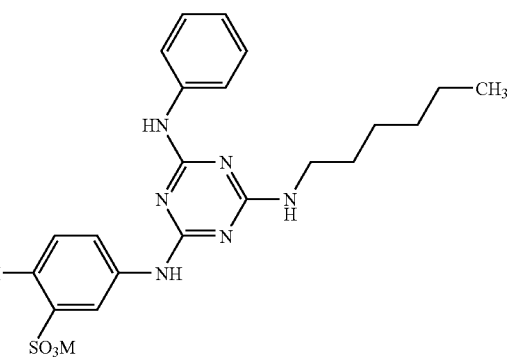

(5)

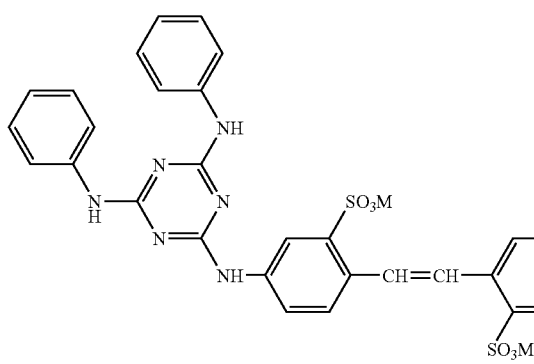
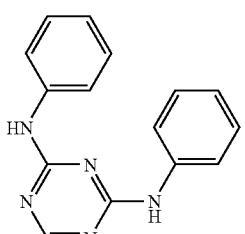

(6)

(7)
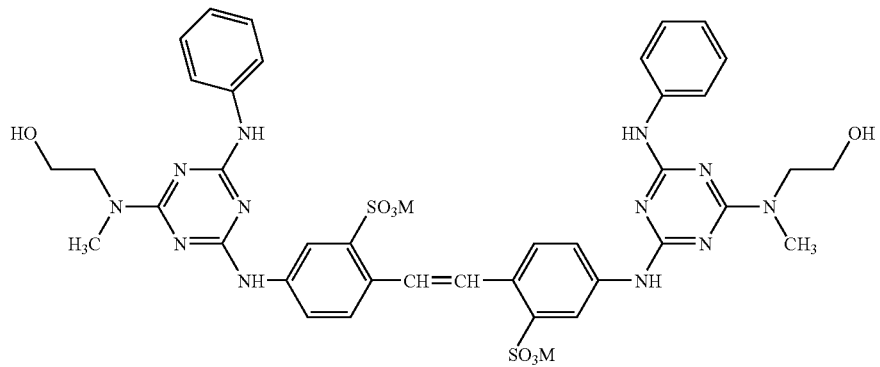
(8)
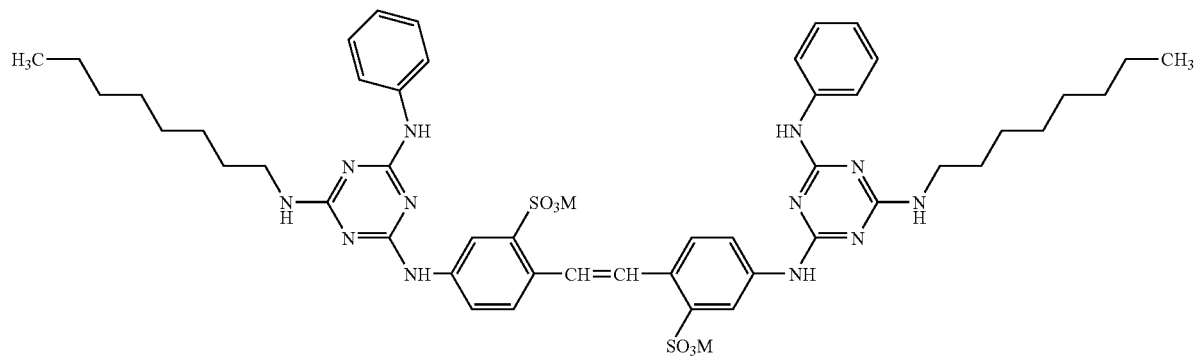
(9)
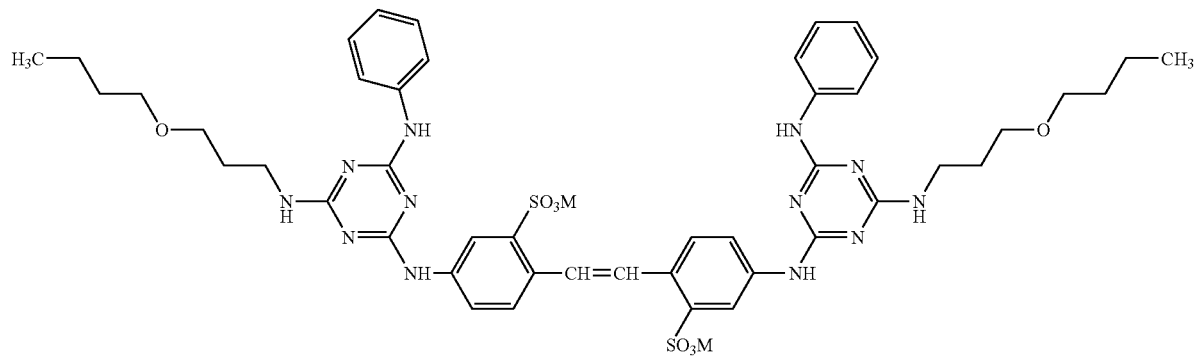
(10)
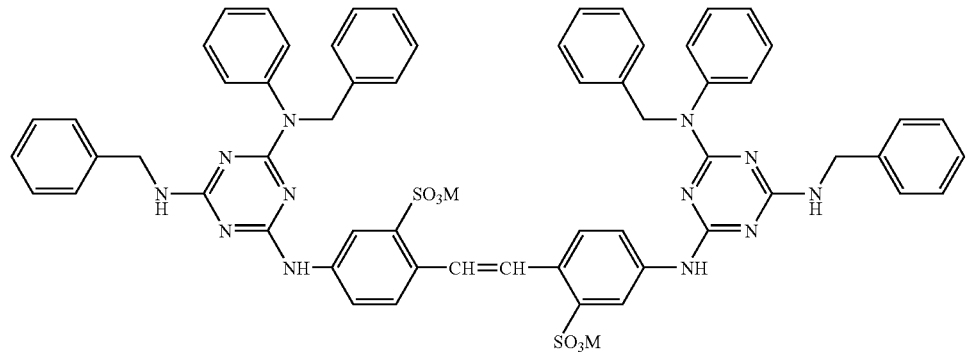

-continued
(11)
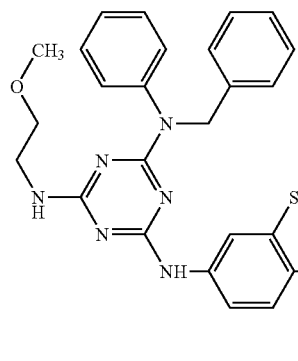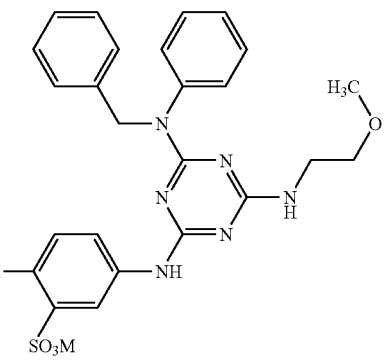
(12)
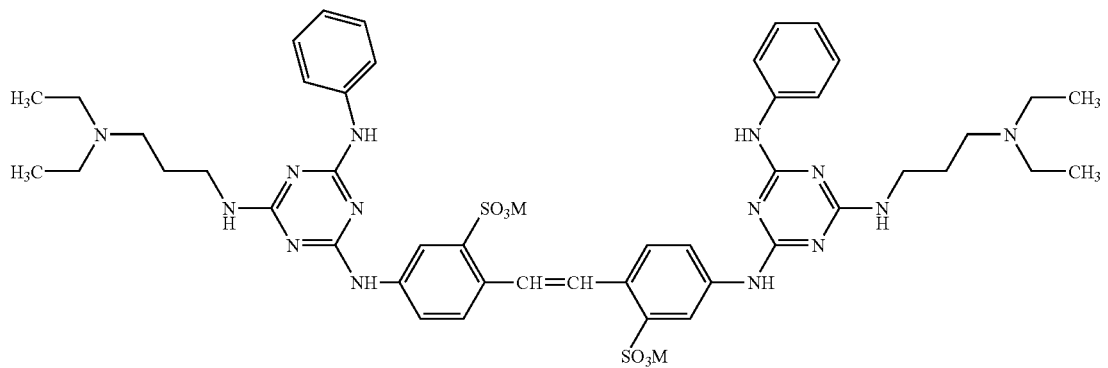
(13)
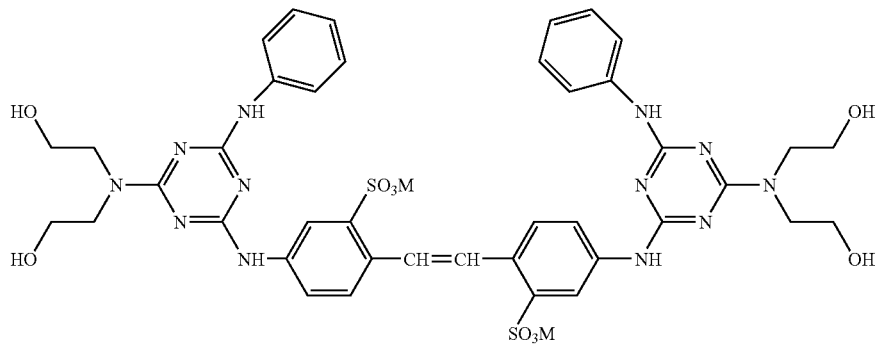
(14)
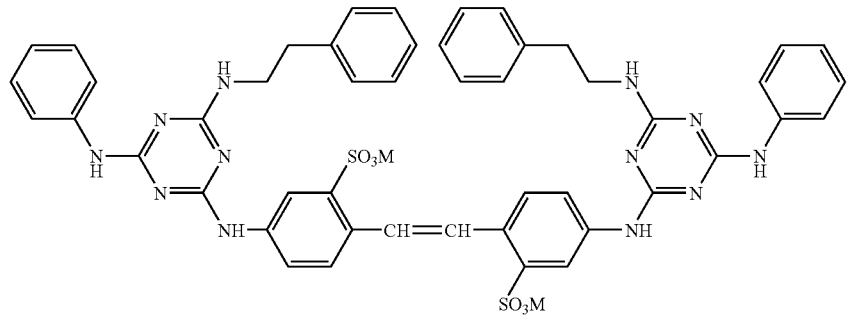

-continued
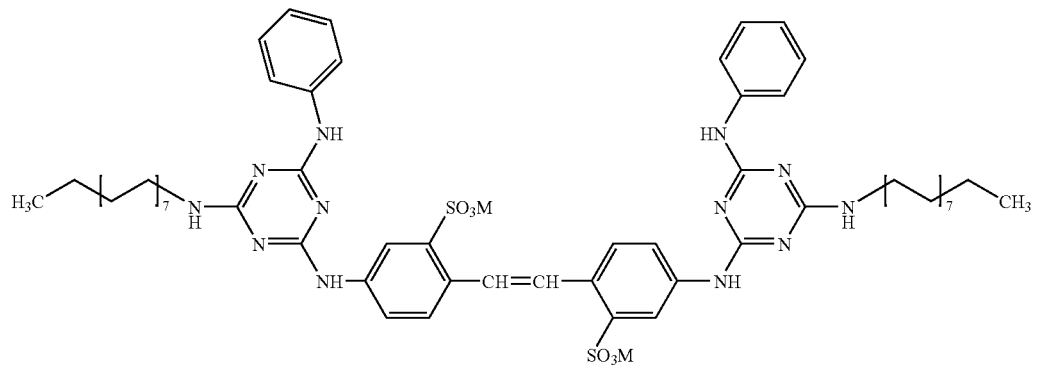
(15)
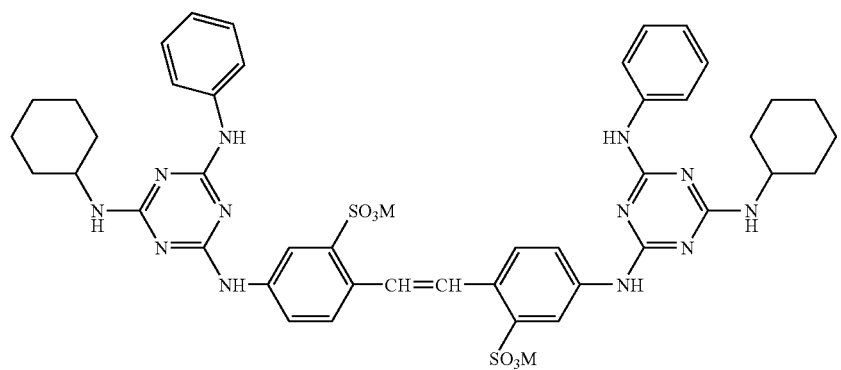
(16)
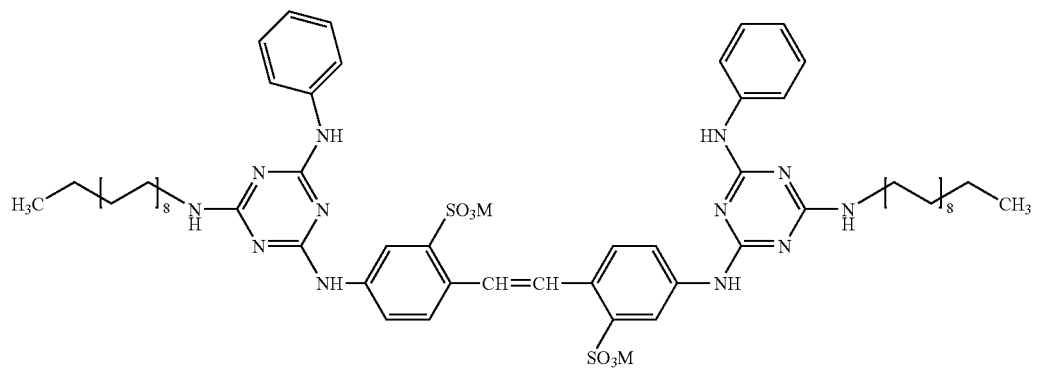
(17)
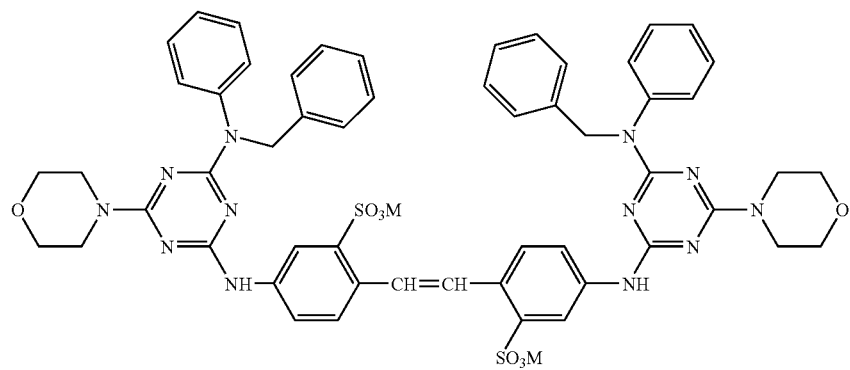
(18)

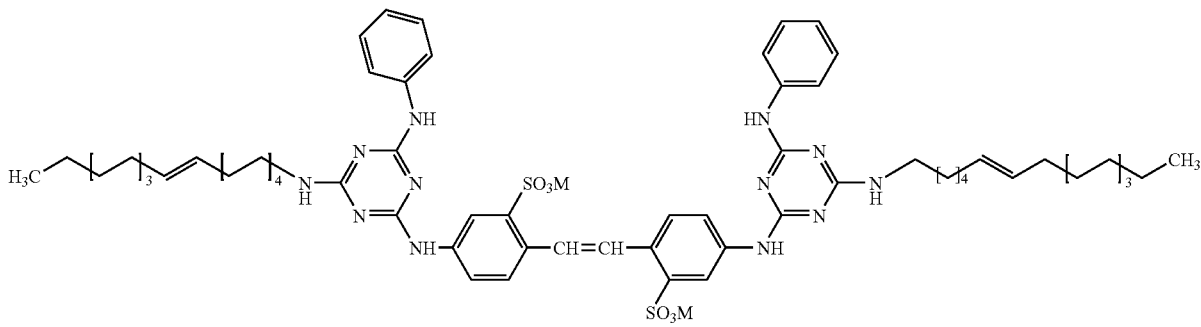

(19)

As well as the use of the components described above, the present invention further encompasses a corresponding brightening process by laundering, as well as processes for the preparation of detergent or softener compositions used in such a process.

A further embodiment of the present invention pertains to a novel fluorescent whitener compound of formula (30)

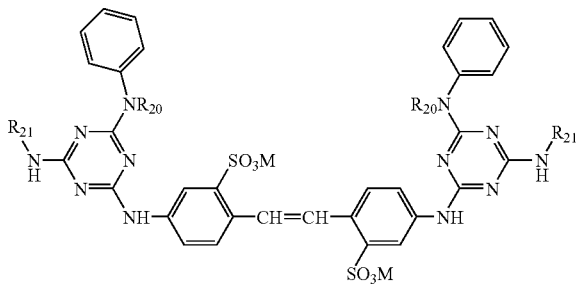

(30)

wherein $R_{20}$ is hydrogen, or substituted or unsubstituted aryl, aralkyl or N-aryl-aralkyl; and $R_{21}$ is substituted, unsubstituted, saturated or unsaturated, branched, unbranched, interrupted or uninterrupted $C_6$-$C_{40}$alkyl, preferably $C_8$-$C_{40}$alkyl, more preferably $C_{12}$-$C_{40}$alkyl, $C_6$-$C_{40}$alkylen, preferably $C_8$-$C_{40}$alkylen, more preferably $C_{12}$-$C_{40}$alkylen, $C_1$-$C_{40}$dialkyl, preferably $C_8$-$C_{40}$dialkyl, more preferably $C_{12}$-$C_{40}$dialkyl, $C_1$-$C_6$dialkylen, preferably $C_8$-$C_{40}$dialkylen, more preferably $C_{12}$-$C_{40}$dialkylen; substituted or unsubstituted aralkyl; and M is a cation.

A further embodiment of the present invention concerns a detergent composition for brightening synthetic, single or blended textile, comprising a fluorescent whitening agent according to formula (30) and a cationic polymer as defined herein before. As described above, especially preferred textiles are polyester or polyamide textiles or polyester or polyamide blended textiles, wherein the blended textile preferably comprises at least 40% by weight, preferably at least 50% by weight, of polyester or polyamide, In addition, the present invention concerns a liquid detergent composition for brightening synthetic, single or blended textile, especially polyester or polyamide textiles or polyester or polyamide blended textiles, wherein the blended textile preferably comprises at least 40% by weight, preferably at least 50% by weight, of polyester or polyamide, comprising a fluorescent whitening agent according to formula (30) and a cationic polymer as defined herein before.

Further, the present invention concerns a softening composition for brightening synthetic, single or blended textile, especially polyester or polyamide textiles or polyester or polyamide blended textiles, wherein the blended textile preferably comprises at least 40% by weight, preferably at least 50% by weight, of polyester or polyamide, comprising a fluorescent whitening agent according to formula (30) and a cationic polymer as defined herein before.

Further, the present invention concerns a detergent composition for brightening a synthetic textile, single or blended textile, especially a polyester or polyamide textile, or polyester or polyamide blended textile, comprising a brightening agent as defined hereinbelow.

Usually, the detergent composition comprises on 100 parts by weight of cationic polymer, 0.1 to 1000, especially 1 to 200, and more especially 10 to 80, parts by weight of free fluorescent whitening agent and 0 to 2000, especially 400 to 1500, parts by weight of water. It can be a liquid or powdery solid composition.

In addition, the present invention concerns a softening composition for brightening synthetic, single or blended textile, especially polyester or polyamide textiles or polyester or polyamide blended textiles, wherein the blended textile preferably comprises at least 40% by weight, preferably at least 50% by weight, of polyester or polyamide, comprising a brightening agent and a cationic polymer as defined hereinbelow.

The softening composition comprises common fabric softener compounds as well as mixtures of fabric softener compounds.

(i) Cationic quaternary ammonium salts. The counter ion of such cationic quaternary ammonium salts may be a halide, such as chloride or bromide, methyl sulphate, or other ions well known in the literature. Preferably the counter ion is methyl sulfate or any alkyl sulfate or any halide, methyl sulfate being most preferred for the dryer-added articles of the invention.

Examples of cationic quaternary ammonium salts include but are not limited to:

(1) Acyclic quaternary ammonium salts having at least two $C_8$ to $C_{30}$, preferably $C_{12}$ to $C_{22}$ alkyl or alkenyl chains, such as: ditallowdimethyl ammonium methylsulfate, di(hydrogenated tallow)dimethyl ammonium methylsulfate, di(hydrogenated tallow)dimethyl ammonium methylchloride, distearyldimethyl ammonium methyl-sulfate, dicocodimethyl ammonium methylsulfate and the like. It is especially preferred if the fabric softening compound is a water insoluble quaternary ammonium material which comprises a compound having two $C_{12}$ to $C_{18}$ alkyl or alkenyl groups connected to the molecule via at least one ester link. It is more preferred if the quaternary ammonium material has two ester links present. An especially preferred ester-linked quaternary ammonium material for use in the invention can be represented by the formula:

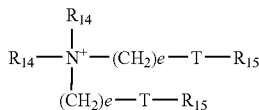

wherein each $R_{14}$ group is independently selected from $C_1$ to $C_4$ alkyl, hydroxyalkyl or $C_2$ to $C_4$ alkenyl groups; T is either —O—C(O)— or —C(O)—O—, and wherein each $R_{15}$ group is independently selected from $C_8$ to $C_{28}$ alkyl or alkenyl groups; and e is an integer from 0 to 5.

A second preferred type of quaternary ammonium material can be represented by the formula:

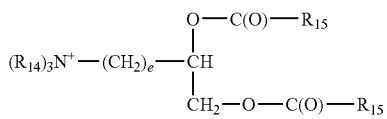

wherein $R_{14}$, e and $R_{15}$ are as defined above.

(2) Cyclic quaternary ammonium salts of the imidazolinium type such as di(hydrogenated tallow)dimethyl imidazolinium methylsulfate, 1-ethylene-bis(2-tallow-1-methyl) imidazolinium methylsulfate and the like;

(3) Diamido quaternary ammonium salts such as: methylbis(hydrogenated tallow amidoethyl)-2-hydroxethyl ammonium methyl sulfate, methyl bi(tallowamidoethyl)-2-hydroxypropyl ammonium methylsulfate and the like;

(4) Biodegradable quaternary ammonium salts such as N,N-di(tallowoyl-oxy-ethyl)N,N-dimethyl ammonium methyl sulfate and N,N-di(tallowoyl-oxy-propyl)-N,N-dimethyl ammonium methyl sulfate. Biodegradable quaternary ammonium salts are described, for example, in U.S. Pat. Nos. 4,137,180, 4,767,547 and 4,789,491 incorporated by reference herein.

Preferred biodegradable quaternary ammonium salts include the biodegradable cationic diester compounds as described in U.S. Pat. No. 4,137,180, herein incorporated by reference.

(ii) Tertiary fatty amines having at least one and preferably two $C_8$ to $C_{30}$, preferably $C_{12}$ to $C_{22}$ alkyl chains. Examples include hardened tallow-di-methylamine and cyclic amines such as 1-(hydrogenated tallow)amidoethyl-2-(hydrogenated tallow) imidazoline. Cyclic amines, which may be employed for the compositions herein, are described in U.S. Pat. No. 4,806,255 incorporated by reference herein.

(iii) Carboxylic acids having 8 to 30 carbons atoms and one carboxylic group per molecule. The alkyl portion has 8 to 30, preferably 12 to 22 carbon atoms. The alkyl portion may be linear or branched, saturated or unsaturated, with linear saturated alkyl preferred. Stearic acid is a preferred fatty acid for use in the composition herein. Examples of these carboxylic acids are commercial grades of stearic acid and palmitic acid, and mixtures thereof, which may contain small amounts of other acids.

(iv) Esters of polyhydric alcohols such as sorbitan esters or glycerol stearate. Sorbitan esters are the condensation products of sorbitol or iso-sorbitol with fatty acids such as stearic acid. Preferred sorbitan esters are monoalkyl. A common example of sorbitan ester is SPAN® 60 (ICI) which is a mixture of sorbitan and isosorbide stearates.

(v) Fatty alcohols, ethoxylated fatty alcohols, alkylphenols, ethoxylated alkylphenols, ethoxylated fatty amines, ethoxylated monoglycerides and ethoxylated diglycerides.

(vi) Mineral oils, and polyols such as polyethylene glycol.

These softeners are more definitively described in U.S. Pat. No. 4,134,838 the disclosure of which is incorporated by reference herein. Preferred fabric softeners for use herein are acyclic quaternary ammonium salts. Mixtures of the above mentioned fabric softeners may also be used.

The softening composition employed in the present invention preferably contains about 0.1 to about 95 wt-%, based on the total weight of the fabric softening composition, of the fabric softening component. Preferred is an amount of 0.5 to 50 wt-%, especially an amount of 2 to 50 wt-% and most preferably an amount of 2 to 30 wt-%.

The fabric softening composition may also comprise additives which are customary for standard commercial fabric softening compositions, for example alcohols, such as ethanol, n-propanol, i-propanol, polyhydric alcohols, for example glycerol and propylene glycol; amphoteric and nonionic surfactants, for example carboxyl derivatives of imidazole, oxyethylated fatty alcohols, hydrogenated and ethoxylated castor oil, alkyl polyglycosides, for example decyl polyglucose and dodecylpolyglucose, fatty alcohols, fatty acid esters, fatty acids, ethoxylated fatty acid glycerides or fatty acid partial glycerides; also inorganic or organic salts, for example water-soluble potassium, sodium or magnesium salts, non-aqueous solvents, pH buffers, perfumes, chelating agents, dyes, hydrotropic agents, antifoams, anti redeposition agents, enzymes, optical brighteners, antishrink agents, stain removers, germicides, fungicides, dye fixing agents or dye transfer inhibitors (as described in WO-A-02/02865), antioxidants, corrosion inhibitors, wrinkle recovery or wet soiling reduction agent, such as polyorganosiloxanes. The latter two additives are described in WO0125385.

Such additives are preferably used in an amount of 0 to 30 wt-%, based on the total weight of the fabric softening composition. Preferred is an amount of 0 to 20 wt-%, especially an amount of 0 to 10 wt-% and most preferably an amount of 0 to 5 wt-%.

The fabric softener compositions are preferably in liquid aqueous form. The fabric softener compositions preferably contain a water content of 25 to 90 wt-% based on the total weight of the composition. More preferably, the water content is 50 to 90 wt-%, especially 60 to 90 wt-%.

The fabric softener compositions preferably have a pH value from 2.0 to 9.0, especially 2.0 to 5.0.

The softening composition may be solid or liquid. Preferred is a liquid softening composition. Usually, the softening composition comprises on 100 parts by weight of cationic polymer, 0.1 to 1000, especially 1 to 200, more especially 10 to 80, parts by weight of a free fluorescent whitening agent and 0 to 2000, especially 400 to 1500, parts by weight of water.

The softening composition often contains further ingredients known in the art.

The weight ratio of cationic polymer to fluorescent whitening agent in the detergent composition, the liquid detergent composition or the softening composition is in the range from 1:10 to 1000:1, preferably from 1:2 to 10:1 (cationic polymer: fluorescent whitening agent).

The detergent may be formulated as a solid, or as an aqueous liquid comprising, e.g., 5-50, preferably 10-35% water or as a non-aqueous liquid detergent, containing not more than 5, preferably 0-1 wt. % of water, and based on a suspension of a builder in a non-ionic surfactant, as described, e.g., in GB-A-2158454.

The anionic surfactant component may be, e.g., an alkylbenzenesulfonate, an alkylsulfate, an alkylethersulfate, an olefinsulfonate, an alkanesulfonate, a fatty acid salt, an alkyl or alkenyl ether carboxylate or a sulfofatty acid salt or an ester thereof. Preferred are alkylbenzenesulfonates having 10 to 20 carbon atoms in the alkyl group, alkylsulfates having 8 to 18 carbon atoms, alkylethersulfates having 8 to 18 carbon atoms, and fatty acid salts being derived from palm oil or tallow and having 8 to 18 carbon atoms. The average molar number of ethylene oxide added in the alkylethersulfate is preferably 1 to 20, preferably 1 to 10. The salts are preferably derived from an alkalinene metal like sodium and potassium, especially sodium. Highly preferred carboxylates are alkaline metal sarcosinates of formula R—CO($R^1$)$CH_2COOM^1$ in which R is alkyl or alkenyl having 9-17 carbon atoms in the alkyl or alkenyl radical, $R^1$ is $C_1$-$C_4$ alkyl and $M^1$ is alkaline metal, especially sodium.

The nonionic surfactant component may be, e.g., primary and secondary alcohol ethoxylates, especially the $C_8$-$C_{20}$ aliphatic alcohols ethoxylated with an average of from 1 to 20 moles of ethylene oxide per mole of alcohol, and more especially the $C_{10}$-$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

The total amount of anionic surfactant and nonionic surfactant is preferably 5-50% by weight, preferably 540% by weight and more preferably 5-30% by weight. As to these surfactants it is preferred that the lower limit is 10% by weight.

The builder component may be an alkaline metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly(alkylene phosphonate); or a mixture of these.

Preferred silicates are crystalline layered sodium silicates of the formula $NaHSi_mO_{2m+1} \cdot pH_2O$ or $Na_2Si_mO_{2m+1} \cdot pH_2O$ in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkaline metal ethane 1-hydroxy diphosphonates, nitrilo trimethylene phosphonates, ethylene diamine tetra methylene phosphonates and diethylene triamine penta methylene phosphonates.

The amount of builders is preferably 5-70% by weight, preferably 5-60% by weight and more preferably 10-60% by weight. As to the builders it is preferred that the lower limit is 15% by weight, especially 20% by weight.

Suitable peroxide components include, for example, the organic and inorganic peroxides (like sodium peroxides) known in the literature and available commercially that bleach textile materials at conventional washing temperatures, for example at from 5 to 95° C.

In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides.

The amount of peroxide is preferably 0.5-30% by weight, preferably 1-20% by weight and more preferably 1-15% by weight. In case a peroxide is used, the lower limit is preferably 2% by weight, especially 5% by weight.

Furthermore, the detergent can optionally contain enzymes. Enzymes can be added to detergents for stain removal. The enzymes usually improve the performance on stains that are either protein- or starch-based, such as those caused by blood, milk, grass or fruit juices. Preferred enzymes are cellulases, proteases, amylases and lipases. Preferred enzymes are cellulases and proteases, especially proteases. Cellulases are enzymes, which act on cellulose and its derivatives and hydrolyze them into glucose, cellobiose, cellooligosaccharide. Cellulases remove dirt and have the effect of mitigating the roughness to the touch. Examples of enzymes to be used include, but are by no means limited to, the following:

proteases as given in U.S. Pat. No. 6,242,405, column 14, lines 21 to 32;

lipases as given in U.S. Pat. No. 6,242,405, column 14, lines 33 to 46;

amylases as given in U.S. Pat. No. 6,242,405, column 14, lines 47 to 56; and cellulases as given in U.S. Pat. No. 6,242,405, column 14, lines 57 to 64.

The enzymes can optionally be present in the detergent. When used, the enzymes are usually present in an amount of 0.01-5% by weight, preferably 0.05-5% and more preferably 0.1-4% by weight, based on the total weight of the detergent.

Further preferred additives for the detergents according to the invention are polymers that, during the washing of textiles, inhibit staining caused by dyes in the washing liquor that have been released from the textiles under the washing conditions (dye fixing agents, dye transfer inhibitors). Such polymers are preferably polyvinylpyrrolidones, polyvinylimidazoles or polyvinylpyridine N-oxides which may have been modified by the incorporation of anionic or cationic substituents, especially those having a molecular weight in the range from 5000 to 60 000, more especially from 10 000 to 50 000. Such polymers are usually used in an amount of from 0.01 to 5%, preferably 0.05 to 5% by weight, especially 0.1 to 2% by weight, based on the total weight of the detergent. Preferred polymers are those given in WO-A-02/02865 (see especially page 1, last paragraph and page 2, first paragraph).

The detergents used will usually contain one or more auxiliaries such as soil suspending agents, for example sodium carboxymethylcellulose; salts for adjusting the pH, for example alkaline or alkalinene earth metal silicates; foam regulators, for example soap; salts for adjusting the spray drying and granulating properties, for example sodium sulphate; perfumes; and also, if appropriate, antistatic and softening agents; such as smectite days; photobleaching agents; pigments; and/or shading agents. These constituents should, of course, be stable to any bleaching system employed. Such auxiliaries can be present in an amount of, for example, 0.1 to 20% by weight, preferably 0.5 to 10% by weight, especially 0.5 to 5% by weight, based on the total weight of the detergent.

The detergent compositions can take a variety of physical forms including powder, granular, tablet and liquid forms. Examples thereof are conventional powder heavy-duty detergents, compact and supercompact heavy-duty detergents and tablets, like heavy-duty detergent tablets. One important physical form is the so-called concentrated granular form adapted to be added to a washing machine.

Of importance are also the so-called compact (or supercompact) detergents. In the field of detergent manufacture, a trend has developed recently towards the production of compact detergents, which contain increased amounts of active substance. In order to minimize energy expenditure during the washing process, the compact detergents are required to operate efficiently at temperatures as low as 40° C., or even at room temperatures, e.g. at 25° C. Such detergents usually contain only low amounts of fillers or processing aids, like sodium sulfate or sodium chloride. The amount of such fillers is usually 0-10% by weight, preferably 0-5% by weight, especially 0-1% by weight, based on the total weight of the detergent. Such detergents usually have a bulk density of 650-1000 g/l, preferably 700-1000 g/l and especially 750-1000 g/l.

The detergents can also be present in the form of tablets. Relevant characteristics of tablets are ease of dispensing and convenience in handling. Tablets are the most compact delivery of solid detergents and have a bulk density of, for example, 0.9 to 1.3 kg/litre. To enable fast disintegration laundering detergent tablets generally contain special disintegrants:

Effervescents such as carbonate/hydrogencarbonate/citric acid;
swelling agents like cellulose, carboxymethyl cellulose, cross-linked poly(N-vinylpyrrollidone);
quickly dissolving materials such as Na(K) acetate, or Na(K) citrate;
rapidly dissolving water-soluble rigid coating such as dicarboxy acids.

The tablets can also contain combinations of any of the above disintegrants.

Non-aqueous liquid detergent compositions can contain other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers. The detergents can also be present as the so-called "unit liquid dose" form.

If desired, the detergent composition, the liquid detergent compositions and softening compositions may contain further components, such as those already described above for the liquid and solid formulations comprising a fluorescent whitening agent.

The process is usually conducted in the temperature range of from 5 to 100 C, especially 5 to 60° C. Preferred is a temperature range of 5 to 40° C., especially 5 to 35° C. and more preferably 5 to 30° C.

The detergent compositions herein will preferably be formulated such that, during use in aqueous cleaning operations, the wash water will have a pH of between about 6.5 and about 11, preferably between about 7.5 and 11. Laundering products are typically at pH 9-11. Techniques for controlling pH at recommended usage levels include the use of buffers, alkalines, acids, etc., and are well known to those skilled in the art.

Machine laundering methods herein typically comprise treating soiled laundering with an aqueous wash solution in a washing machine having dissolved or dispensed therein an effective amount of a machine laundering detergent composition in accordance with the invention. By an effective amount of the detergent composition it is meant, e.g., from 20 g to 300 g of product dissolved or dispersed in a wash solution of volume from 5 to 85 liters, as are typical product dosages and wash solution volumes commonly employed in conventional machine laundering methods. Examples are top-loading, vertical axis U.S.-type automatic washing machines using about 45 to 83 liters of water in the wash bath, a wash cycle of about 10 to about 14 minutes and a wash water temperature of about 10 to about 50° C.;

front-loading, horizontal-axis European-type automatic washing machine using about 8 to 15 liters of water in the wash bath, a wash cycle of about 10 to about 60 minutes and a wash water temperature of about 30 to about 95° C.;

top-loading, vertical-axis Japanese-type automatic washing machine using about 26 to 52 liters of water in the wash bath, a wash cycle of about 8 to about 15 minutes and a wash water temperature of about 5 to about 25° C.

The liquor ratio is preferably, 1:3 to 1:100, especially 1:4 to 1:40, more especially 1:4 to 1:15. Highly preferred is a liquor ratio of 1:4 to 1:10, especially 1:5 to 1:9.

This detergent treatment of textiles can be conducted as a domestic treatment in normal washing machines.

Thus, a process for the preparation of a detergent composition for brightening a synthetic textile, single or blended textile, especially a polyester or polyamide textile, or a polyamide or polyester blended textile, comprises
bringing into contact a free fluorescent whitening agent and a cationic polymer with said detergent composition.

Correspondingly, a process for the preparation of a softening composition for brightening a synthetic textile, single or blended textile, especially a polyester or polyamide textile, or a polyamide or polyester blended textile, comprises
a) bringing into contact a fluorescent whitening agent and a cationic polymer with said softening composition.

In general, components for these compositions may be added together in any sequence; in some cases, however, a certain order may be advantageous, e.g.
the fluorescent whitening agent and the cationic polymer are added to the detergent or softening composition, or,
the fluorescent whitening agent is added to the detergent or softening composition, and then the cationic polymer is added, or
the cationic polymer is added to the detergent or softening composition, and then the fluorescent whitening agent is added.

A process for the preparation of a detergent composition for brightening a synthetic textile, single or blended textile, especially a polyester or polyamide textile, or a polyamide or polyester blended textile, thus comprises
bringing into contact a fluorescent whitening agent and a cationic polymer with said detergent composition.

A process for the preparation of a softening composition for brightening a synthetic textile, single or blended textile, especially a polyester or polyamide textile, or a polyamide or polyester blended textile, thus comprises
bringing into contact a fluorescent whitening agent and a cationic polymer with said softening composition.

Consequently, another object of the present invention is a brightening agent, which comprises a free fluorescent whitening agent and a cationic polymer and optionally water.

If desired, the brightening agent may contain further components, such as those already described above for the liquid and solid formulations comprising a fluorescent whitening agent.

In addition, the present invention concerns a brightening agent for synthetic textiles, single or blended textile, especially a polyester or polyamide or polyester textile, or polyamide blended textile, consisting of a cationic polymer and a free fluorescent whitening agent and optionally water.

Preferred is a brightening agent for synthetic textiles, single or blended textile, especially a polyester or polyamide or polyester textile, or polyamide blended textile, comprising on 100 parts by weight of cationic polymer, 0.1 to 1000, especially 1 to 200, more especially 10 to 200 such as 10 to 80, parts by weight of a free fluorescent whitening agent and 0 to 2000, especially 400 to 1500, parts by weight of water.

Further preferred is a brightening agent for synthetic textiles, single or blended textile, especially a polyester or polyamide textile, or polyester or polyamide blended textile, comprising on 100 parts by weight of cationic polymer, 1 to 50 parts by weight, preferably of 10 to 40 parts by weight of a fluorescent whitening agent.

The process for the preparation of the brightening agent for synthetic textiles, single or blended textile, especially a polyester textile, or polyamide or polyester or polyamide blended textile, of the invention comprises contacting 0.1 to 1000, especially 1 to 200, parts by weight of a free flowing fluorescent whitening agent, or a liquid formulation containing such a free fluorescent whitening agent, with 100 parts by weight of cationic polymer and 0 to 2000, especially 400 to 1500, parts by weight of water.

In general, the addition of the components may be effected in any sequence, e.g. the fluorescent whitening agent is added to the cationic polymer, or the cationic polymer to the fluorescent whitening agent. Preferably, the fluorescent whitening is given to the cationic polymer. The temperature of the preparation is usually in the range of 15 to 35° C., preferably of 19 to 25° C. Preferably, cationic polymer is added to water, and then the fluorescent whitening agent added.

If desired, the brightening agent may contain further components, such as those already described above for the liquid and solid formulations comprising a fluorescent whitening agent, e.g. using such formulations as the source of the free fluorescent whitening agent.

Most preferred feature of the present invention is the use of a combination of the free fluorescent whitening agent, especially a free flowing fluorescent whitening agent, and cationic polymer as a brightening agent for synthetic textiles, especially polyester textiles.

EXAMPLES

Preparation of Compound of Formula (5')

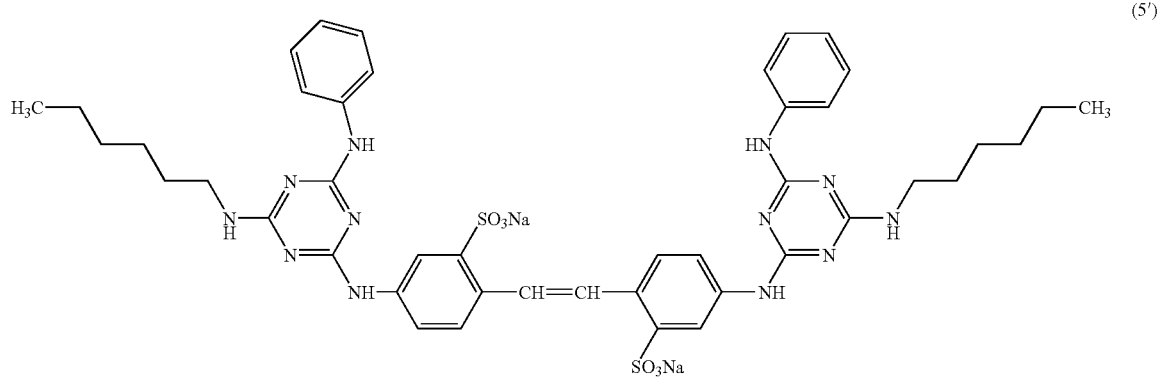

(5')

First Step:

A solution of 18.5 g diaminostilbendisulfoacid-di-sodium salt in 185 ml water is added to a mixture of 130 ml methylethylketon, 80 ml deionate 150 g ice and 18.5 g cyanurchloride in such a rate (about 30 minutes) that the temperature can be kept in the range of −8 to +5° C. and the pH-value can be kept in the range of 4.5 to 5 by simultaneously adding a sodium carbonate solution (20% by weight) is 15% ige sodium carbonate. A yellowish suspension is obtained.

Second Step:

9.2 g anilin added to the suspension, prepared in step 1, in 10 minutes, whereby the ph is kept in the range of 6.8 to 7.5 by simultaneously adding a sodium carbonate solution (20% by weight) is 15% ige sodium carbonate.

After the addition the obtained mixture is warmed to a temperature in the range of 40 to 45° C. The pH value is adjusted in the range of 6.8 to 7.5 by simultaneously adding a sodium carbonate solution (20% by weight), and then the reaction mixture heated to 60° C.

Third Step:

12 g Hexylamine are added to the reaction mixture, obtained in the second step, at 60° C. Then the reaction mixture is heated to 98° C. in about 30 minutes, and 140 ml of a mixture of methylethylketon and water distillated by maintaining the pH value in the range of 8.8 and 9.2 by simultaneously adding sodium hydroxide (16% solution). When the pH value is constant in the range of 8.8 and 9.2 (after about one hour) the reaction mixture is cooled to 30° C. A crude beige suspension is obtained, which is filtrated. The filter residue is dried in vacuum. There are obtained 50.5 g of a yellowish powder of compound of formula (5').

Application Example

The fluorescent whitening agents are incorporated into ECE 77 detergent via formulation at concentrations based on a FWA offer of 64 µmol per kg fabric/wash cycle.

FWA = fluorescent whitening agent
ECE77 (Definition according to ISO 105-CO6; DIN 54017)

| Ingredients | Concentration % |
|---|---|
| LAS ($C_{11.5}$) | 8.0% |
| Nonionics (Tallow-alcohol $EO_{14}$) | 2.9% |
| Soap ($C_{12-16}$ 13-26%, $C_{18-22}$ 74-87%) | 3.5% |
| Sodium tripolyphosphate | 43.8% |
| Sodium silicate ($SiO_2$:$Na_2O$ = 3.3:1) | 7.5% |
| Magnesium silicate | 1.9% |
| CMC | 1.2% |
| EDTA | 0.2% |
| Sodium sulfate | 21.2% |
| Water | 9.8% |

LAS = Linear Alkylbenzolsulfonate
$C_{11.5}$ = average carbonchain of 11.5 carbons
$C_{12-16}$ = average carbonchain in the range of 12 to 16 carbons
$C_{18-22}$ = average carbonchain in the range of 18 to 22 carbons
CMC = Carboxymethylcellulose
EDTA = Ethylendiaminotetra acetic acid The Washing Tests are Done at the Following Conditions:

| | |
|---|---|
| Detergent dosage: | 40 g per kg fabric |
| Liquor ratio: | 10 to 1 |
| Wash temperature: | 40° C. |
| Wash time: | 20 minutes |
| Test fabrics: | 100% Polyester(PES) i.e. No 5-3218 |
| Wash cycles: | 1-3 and 5 |
| Indoor drying: | in the cabinet at 40° C. |

Without and with the addition of 4% by weight of Rheovis® CDP (based on weight of detergent). Rheovis® CDP is an acryl polymer based on liquid dispersion polymer technology.
DeltaWn: Increase of whiteness on non-brightened PES after n wash cycles.
The weight ratios are given in relation to the overall weight of the detergent.

Example 1

Application method as described above with fluorescent whitening agent of formula wherein the following polymers are used:

Example 1a a) 4% by weight Rheovis® CDP is used, and

Example 1b b) 5% by weight Magnafloc® LT 35 (a liquid grade polyelectrolyte of high cationic charge and low-medium molecular weight) is used, and Example 1c c) 5% Zetag® 7125 (a highly cationic organic coagulant supplied in liquid form) used.

| | DeltaW1 | DeltaW3 | DeltaW5 |
|---|---|---|---|
| 4% Rheovis ® CDP (AS 50%) as reference | 19 | 45 | 53 |
| 5% Magnafloc ® LT 35 (AS 40%) | 16 | 44 | 54 |
| 5% Zetag ® 7125 (AS 40%) | 18 | 46 | 54 |

W1 is increase of whiteness on non-brightened polyester after 1 wash cycle.
W2 is increase of whiteness on non-brightened polyester after 2 wash cycles.
W3 is increase of whiteness on non-brightened polyester after 3 wash cycles.

Fluorescent whitening agents of formulae (4) and (6) to (19) are applied according to example 1 of the present application by replacing the fluorescent whitening agent (5). All the tested fluorescent whitening agents exhibit a significant increase of whiteness on non-brightened polyester after one, two and three wash cycles.

The invention claimed is:
1. A laundering process for brightening a polyester or polyester/cotton textile, which is characterized by
   a) preparing a composition by contacting a free fluorescent whitening agent with a cationic polymer and an anionic surfactant
   b) treating said textile with the composition prepared in step a),
   wherein the free fluorescent whitening agent is a compound selected from the group of formulae (4) to (27)

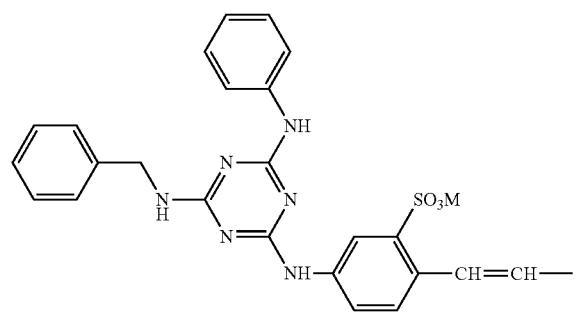
(4)
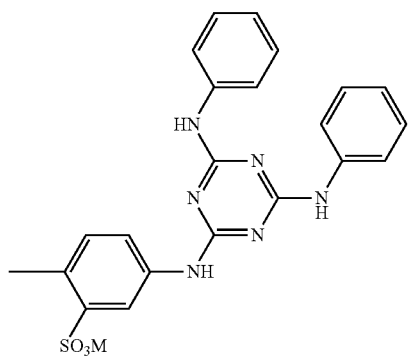
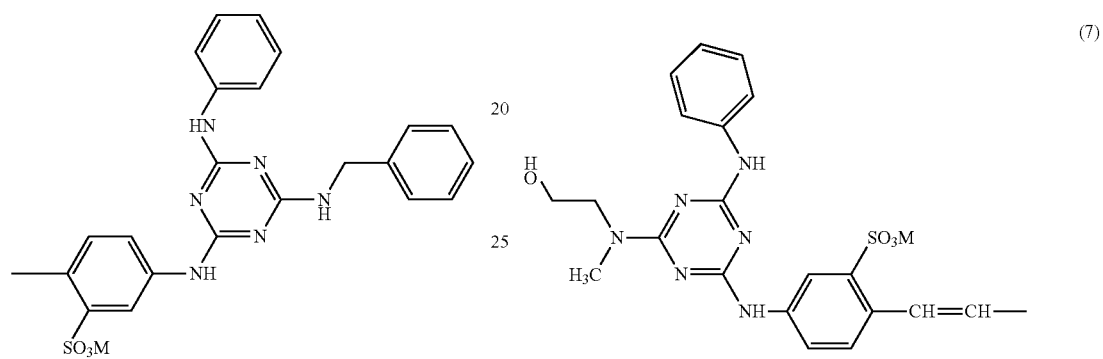
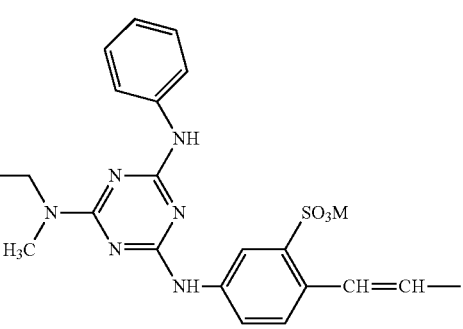
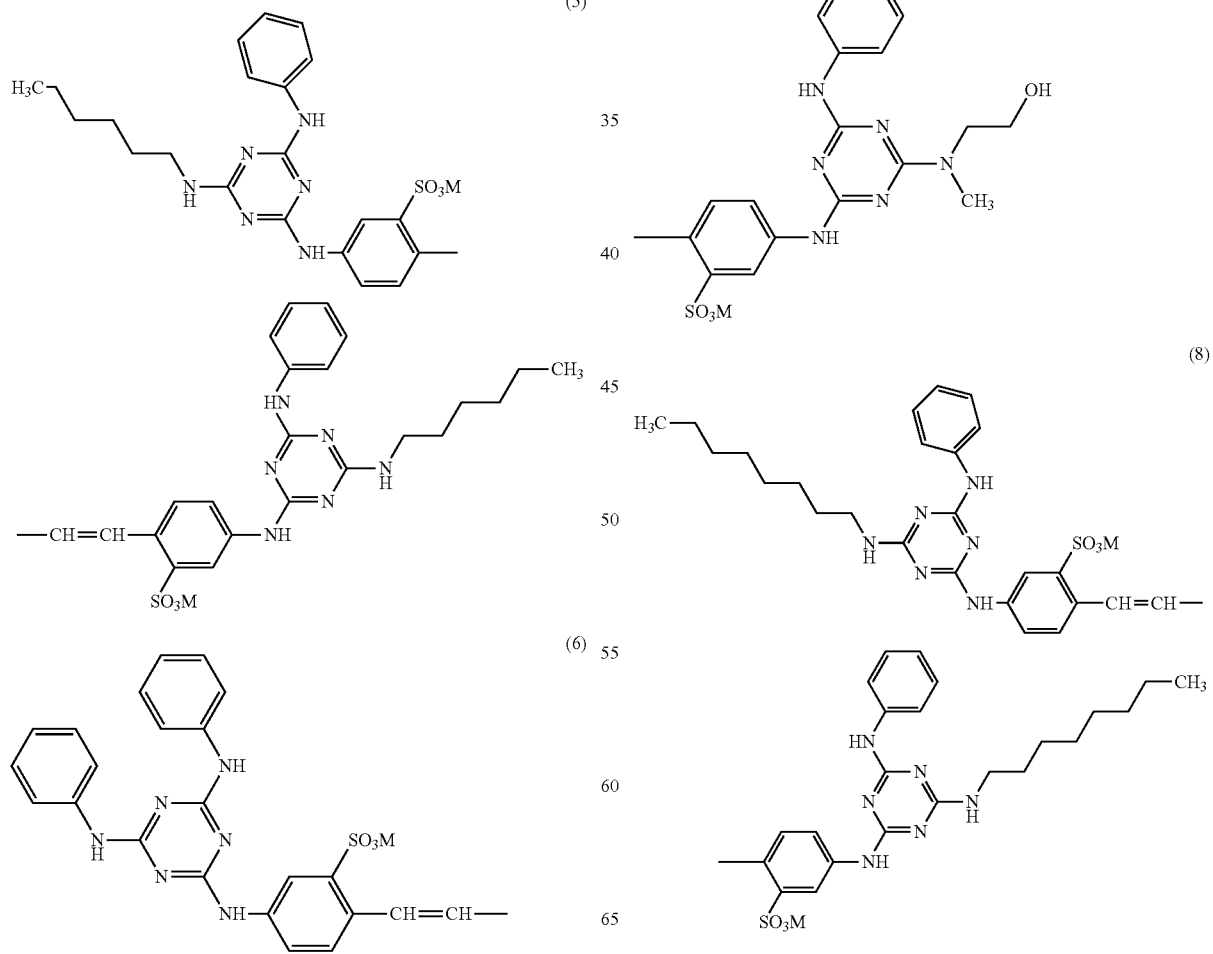

-continued
(9)
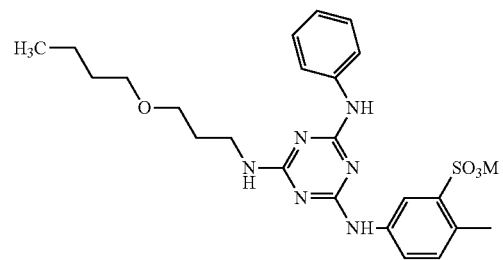
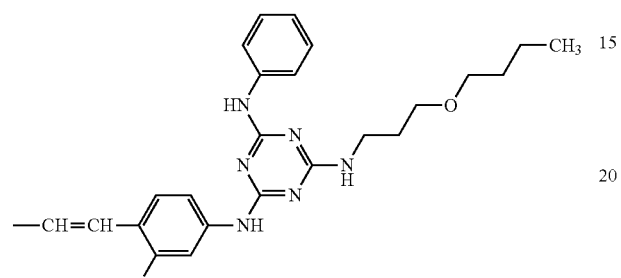
(10)
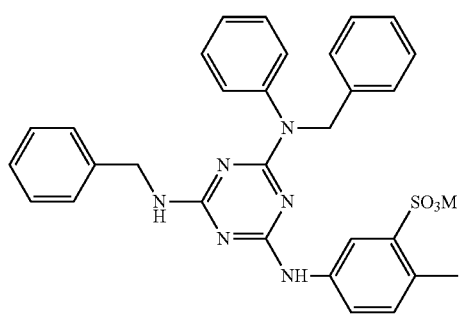
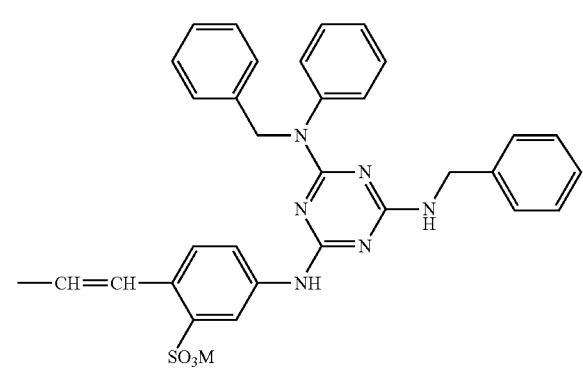
(11)
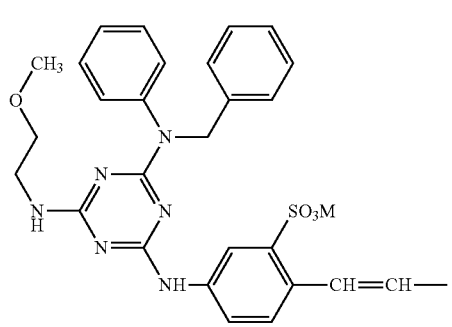
-continued
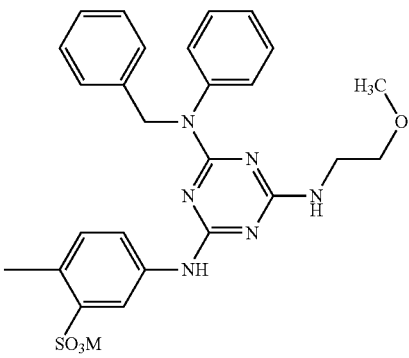
(12)
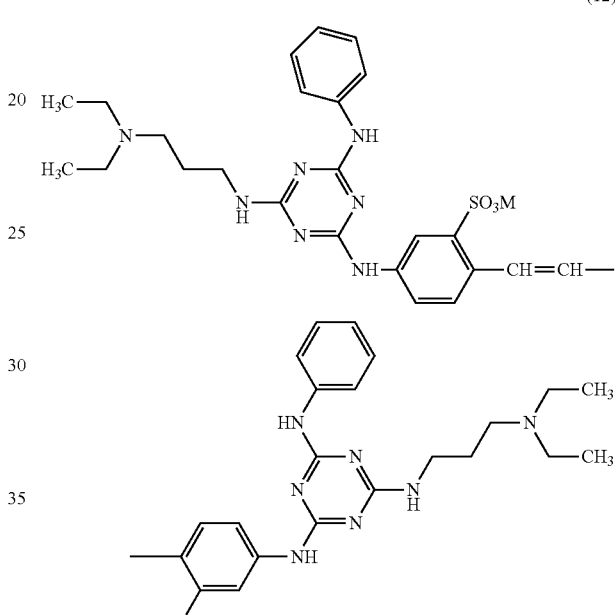
(13)
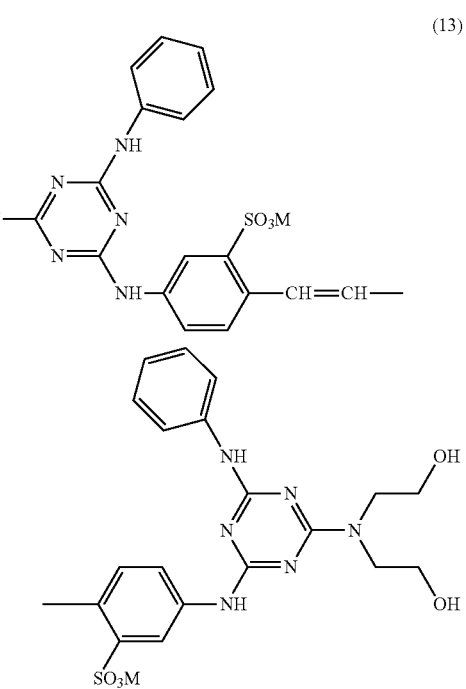

(14)
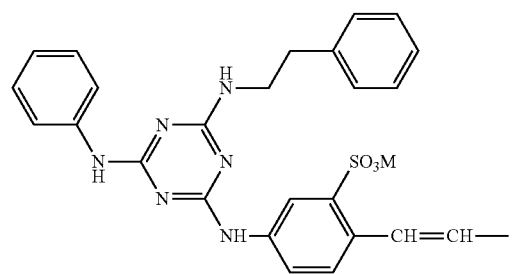
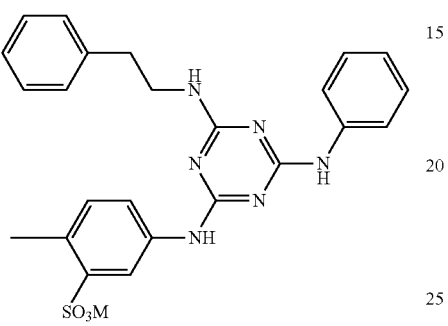
(15)
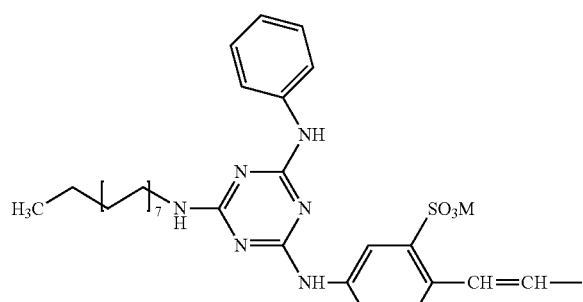
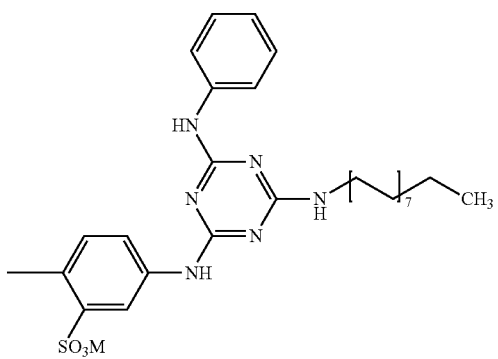
(16)
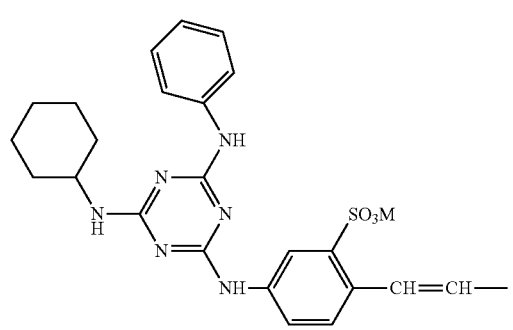
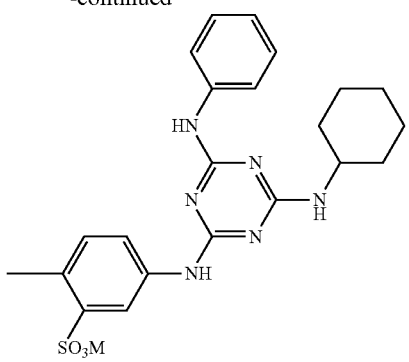
(17)
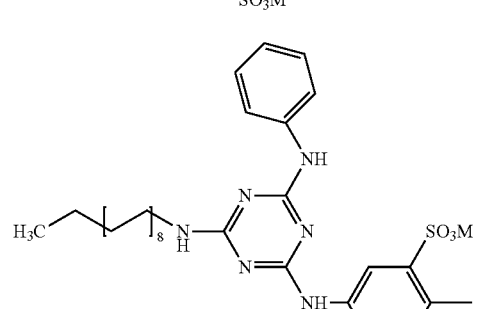
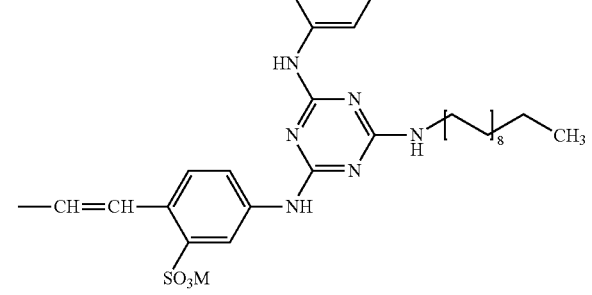
(18)
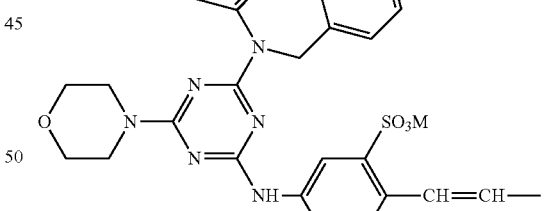
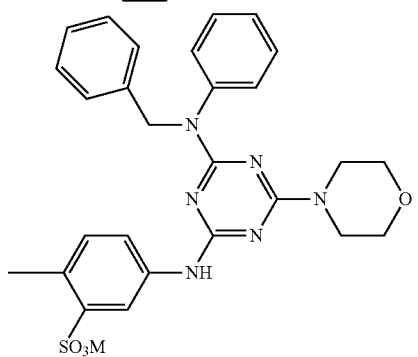

(19)
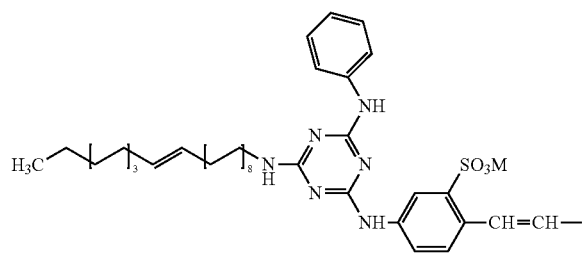
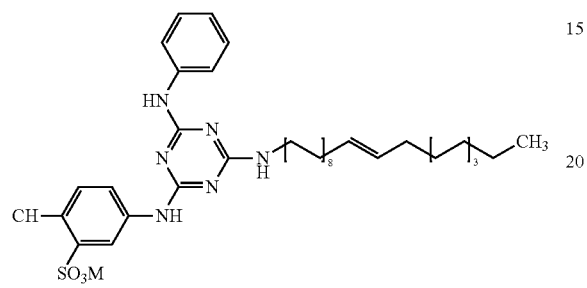
(20)
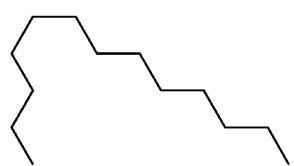
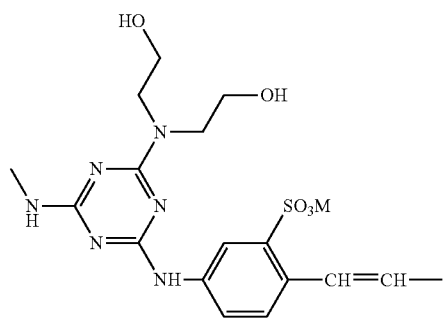
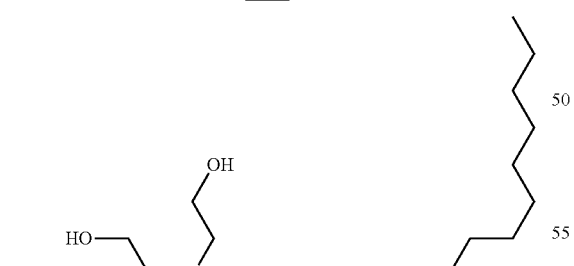
(21)
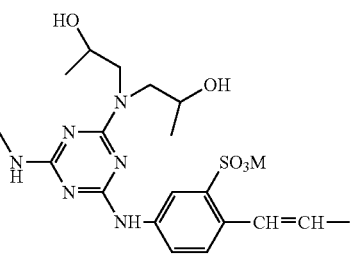
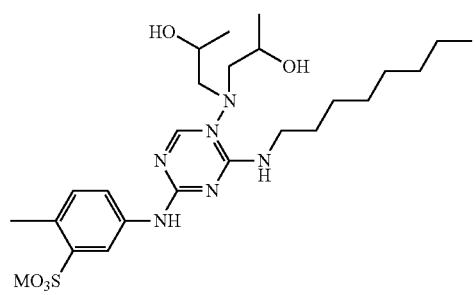
(22)
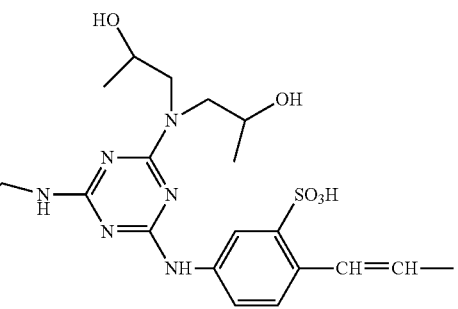
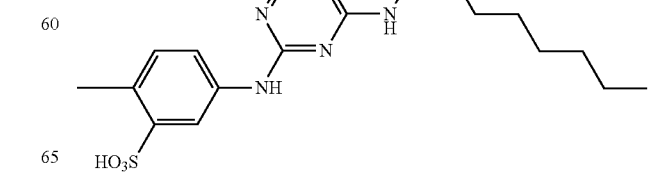

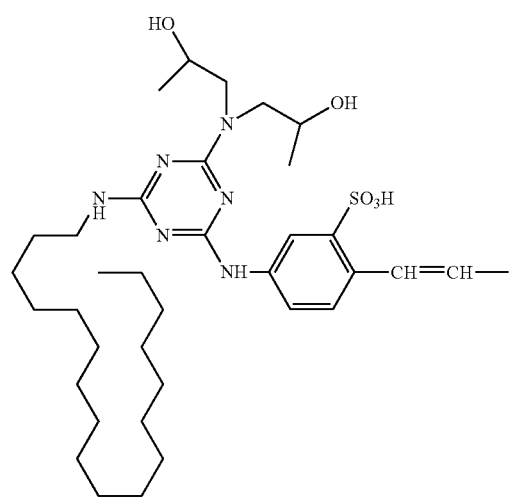
(23)
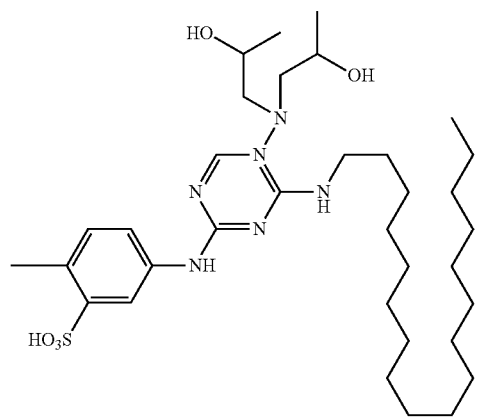
(24)
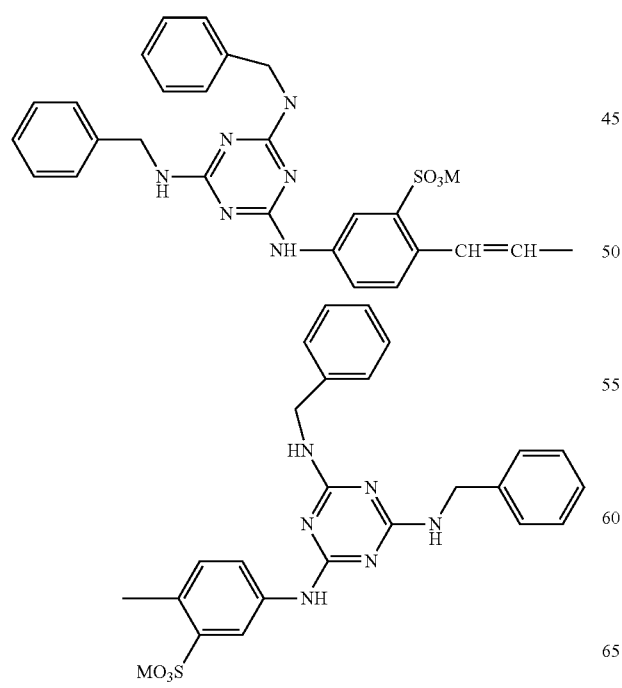
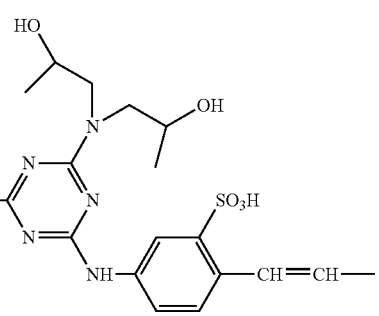
(25)
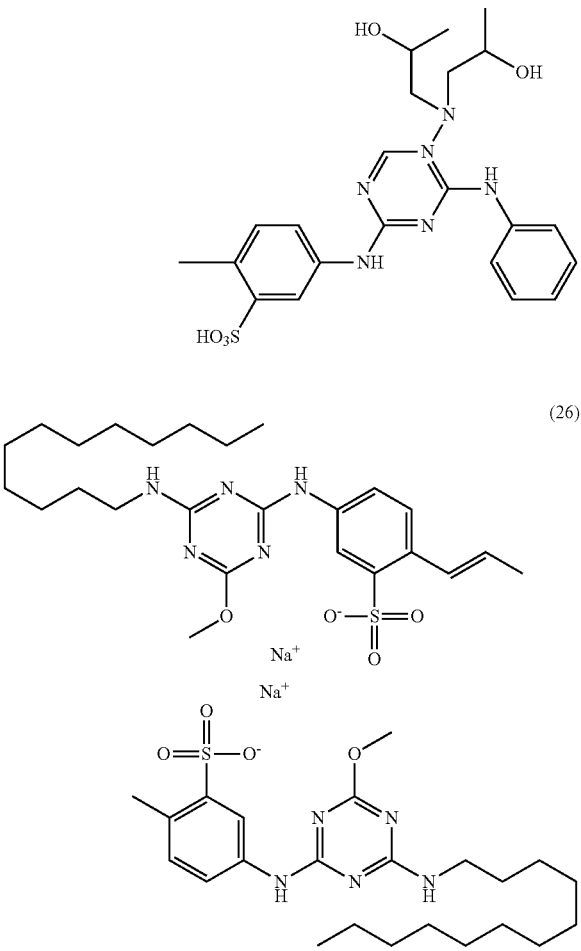
(26)
(27)
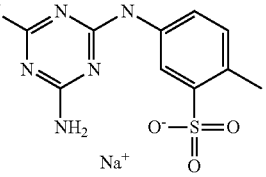

-continued

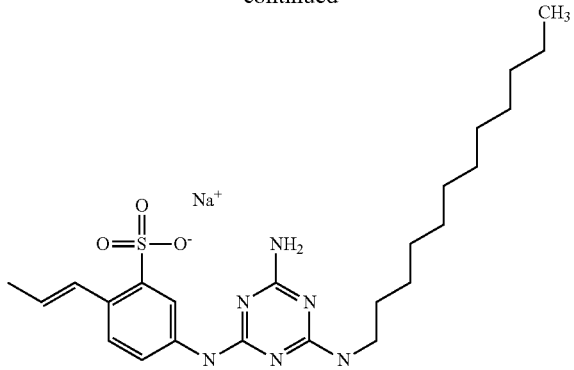

and the cationic polymer is selected from the group consisting of
a liquid dispersion cationic acryl polymer, a cationic homopolymer formed from 2-propen-1-aminium, N,N-dimethyl N-2-propenyl-, chloride and cellulose, 2-hydroxyethyl 2-hydroxy-3-(trimethylammonio)propyl ether, chloride and the fluorescent whitener ranges from 1 to 10 parts by weight per 100 parts of the cationic polymer.

2. A process according to claim 1, wherein the textile is a polyester.

3. A process according to claim 1, wherein the free fluorescent whitening agent is amphiphilic.

4. A process according to claim 1, wherein step a) comprises introducing the free fluorescent whitening agent and the cationic polymer in water.

5. A process according to claim 1, wherein step a) is carried out for initiating a wash cycle.

6. A brightening agent for a polyester or polyester/cotton textile, comprising a cationic polymer and a free fluorescent whitening agent as defined in claim 1 and optionally water.

7. The brightening agent according to claim 6, wherein the free fluorescent whitening agent is a compound of formula (16).

8. The brightening agent according to claim 6, wherein the cationic polymer has a molecular weight within the range from about 2,000 to about 30,000,000.

9. A detergent composition for brightening a polyester or polyester/cotton, comprising a brightening agent as defined in claim 6.

10. The detergent composition according to claim 9 in the form of an aqueous liquid.

11. A detergent composition for brightening a polyester or polyester/cotton textile, comprising a fluorescent whitening agent and a cationic polymer as defined in claim 1.

* * * * *